(12) United States Patent
Kataoka et al.

(10) Patent No.: US 11,497,425 B2
(45) Date of Patent: Nov. 15, 2022

(54) MAGNETIC FIELD MEASUREMENT APPARATUS

(71) Applicant: Asahi Kasei Microdevices Corporation, Tokyo (JP)

(72) Inventors: Makoto Kataoka, Tokyo (JP); Takenobu Nakamura, Tokyo (JP); Shigeki Okatake, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 309 days.

(21) Appl. No.: 16/809,502

(22) Filed: Mar. 4, 2020

(65) Prior Publication Data
US 2020/0281490 A1 Sep. 10, 2020

(30) Foreign Application Priority Data
Mar. 8, 2019 (JP) ............... JP2019-043019
Jan. 17, 2020 (JP) ............... JP2020-006131

(51) Int. Cl.
*G01R 33/02* (2006.01)
*G01R 33/09* (2006.01)
(Continued)

(52) U.S. Cl.
CPC .......... *A61B 5/242* (2021.01); *G01R 33/0011* (2013.01); *G01R 33/0023* (2013.01);
(Continued)

(58) Field of Classification Search
CPC ......... A61B 5/242; A61B 5/243; A61B 5/245; A61B 2562/0223; A61B 2562/04;
(Continued)

(56) References Cited

U.S. PATENT DOCUMENTS 5,642,045 A 6/1997 Keefe
5,764,061 A 6/1998 Asakawa
(Continued)

FOREIGN PATENT DOCUMENTS

EP 1795864 A1 6/2007
JP H01196586 A 8/1989
(Continued)

OTHER PUBLICATIONS

Hu, Chao, et al. "A cubic 3-axis magnetic sensor array for wirelessly tracking magnet position and orientation." IEEE Sensors Journal 10.5 (2010): 903-913. (Year: 2010).*
(Continued)

*Primary Examiner* — Christopher P McAndrew

(57) ABSTRACT

A measurement apparatus is provided, which includes a magnetic sensor array formed by three-dimensionally arranging a plurality of magnetic sensor cells each including a magnetic sensor, and capable of detecting an input magnetic field in three axial directions; a measurement data acquiring section that acquires a plurality of measurement values based on the input magnetic field detected by the magnetic sensor array; a magnetic field calculating section that calculates the input magnetic field based on the measurement values; an error calculating section that calculates a detection error of the input magnetic field, based on the plurality of measurement values and a calculation result obtained by calculating the input magnetic field; and a measurement data selecting section that selects a plurality of measurement values to be used for calculating the input magnetic field by the magnetic field calculating section, from among the plurality of measurement values, based on the detection error.

14 Claims, 17 Drawing Sheets

US 11,497,425 B2
Page 2

(51) Int. Cl.
*G01R 33/00* (2006.01)
*A61B 5/242* (2021.01)
*A61B 5/243* (2021.01)
*A61B 5/245* (2021.01)

(52) U.S. Cl.
CPC ..... *G01R 33/0094* (2013.01); *G01R 33/0206* (2013.01); *G01R 33/091* (2013.01); *A61B 5/243* (2021.01); *A61B 5/245* (2021.01); *A61B 2562/0223* (2013.01); *A61B 2562/046* (2013.01)

(58) Field of Classification Search
CPC ............ G01R 33/0011; G01R 33/0023; G01R 33/0094; G01R 33/0206; G01R 33/091; G01R 33/0041
USPC .......................................................... 600/409
See application file for complete search history.

(56) References Cited

U.S. PATENT DOCUMENTS

| | | | |
|---|---|---|---|
| 2001/0009975 A1 | 7/2001 | Tsukada | |
| 2001/0026222 A1 | 10/2001 | Canady | |
| 2003/0011767 A1 | 1/2003 | Imura | |
| 2004/0155644 A1* | 8/2004 | Stauth | G01R 15/207 324/117 R |
| 2004/0207396 A1 | 10/2004 | Xiao | |
| 2004/0232912 A1 | 11/2004 | Sukamoto | |
| 2005/0030018 A1 | 2/2005 | Shibahara | |
| 2005/0212515 A1 | 9/2005 | Watanabe | |
| 2006/0031038 A1 | 2/2006 | Simola | |
| 2006/0055402 A1* | 3/2006 | Seki | A61B 5/061 324/262 |
| 2006/0066295 A1 | 3/2006 | Tamura | |
| 2007/0108962 A1 | 5/2007 | Taulu | |
| 2008/0161714 A1 | 7/2008 | Ahonen | |
| 2008/0294386 A1 | 11/2008 | Taulu | |
| 2009/0069661 A1 | 3/2009 | Taulu | |
| 2009/0184709 A1 | 7/2009 | Kajola | |
| 2010/0327862 A1* | 12/2010 | Nagasaka | A61B 5/243 324/244.1 |
| 2012/0298239 A1 | 11/2012 | Hodgson | |
| 2013/0109954 A1 | 5/2013 | Simola | |
| 2013/0150702 A1 | 6/2013 | Hokari | |
| 2013/0165766 A1 | 6/2013 | Nishikawa | |
| 2014/0111197 A1 | 4/2014 | Lortie | |
| 2014/0343882 A1 | 11/2014 | Taulu | |
| 2015/0145625 A1 | 5/2015 | Fukasawa | |
| 2015/0253412 A1 | 9/2015 | Jost | |
| 2016/0037277 A1 | 2/2016 | Matsumoto | |
| 2016/0041006 A1 | 2/2016 | Ausserlechner | |
| 2017/0090003 A1 | 3/2017 | Guo | |
| 2017/0100051 A1* | 4/2017 | Honkura | A61B 5/05 |
| 2017/0212188 A1 | 7/2017 | Kikitsu | |
| 2017/0219661 A1 | 8/2017 | Hata | |
| 2017/0299662 A1 | 10/2017 | Nagasaka | |
| 2017/0299663 A1 | 10/2017 | Nagasaka | |
| 2018/0014738 A1 | 1/2018 | Tanaka | |
| 2018/0193728 A1 | 7/2018 | Bashkirov | |
| 2018/0242865 A1 | 8/2018 | Yamagata | |
| 2018/0284310 A1 | 10/2018 | Kawano | |

FOREIGN PATENT DOCUMENTS

| | | |
|---|---|---|
| JP | H05232202 A | 9/1993 |
| JP | 2000051169 A | 2/2000 |
| JP | 2000217798 A | 8/2000 |
| JP | 2000284032 A | 10/2000 |
| JP | 2001083224 A | 3/2001 |
| JP | 2001087237 A | 4/2001 |
| JP | 2002272695 A | 9/2002 |
| JP | 2003199723 A | 7/2003 |
| JP | 2004271303 A | 9/2004 |
| JP | 2005049179 A | 2/2005 |
| JP | 2005195376 A | 7/2005 |
| JP | 2005217341 A | 8/2005 |
| JP | 2006047080 A | 2/2006 |
| JP | 2008032562 A | 2/2008 |
| JP | 2008142154 A | 6/2008 |
| JP | 2011220977 A | 11/2011 |
| JP | 2012152514 A | 8/2012 |
| JP | 2012152515 A | 8/2012 |
| JP | 2013217690 A | 10/2013 |
| JP | 2014134388 A | 7/2014 |
| JP | 2014153054 A | 8/2014 |
| JP | 2014153309 A | 8/2014 |
| JP | 2015075465 A | 4/2015 |
| JP | 2016183944 A | 10/2016 |
| JP | 2017003312 A | 1/2017 |
| JP | 2017026312 A | 2/2017 |
| JP | 2017062122 A | 3/2017 |
| JP | 6153387 B2 | 6/2017 |
| JP | 2017133933 A | 8/2017 |
| JP | 2017166921 A | 9/2017 |
| JP | 2018004618 A | 1/2018 |
| JP | 2018054461 A | 4/2018 |
| WO | 03046587 A1 | 6/2003 |
| WO | 2005030051 A1 | 4/2005 |
| WO | 2017209273 A1 | 12/2017 |

OTHER PUBLICATIONS

Three-Axis Magnetic Sensor HMC1043 Datasheet (Year: 2012).*
Office Action issued for counterpart Japanese Application No. 2018-157607, issued by the Japan Patent Office dated Oct. 23, 2018 (drafted on Oct. 12, 2018).
Office Action issued for counterpart Japanese Application No. 2018-157607, issued by the Japan Patent Office dated Jan. 29, 2019 (drafted on Jan. 23, 2019).
ISA/237) Written Opinion of the International Search Authority for International Patent Application No. PCT/JP2019/050826, issued/mailed by the Japan Patent Office dated Mar. 17, 2020.
Koichiro Kobayashi et al.,"Development of Biomagnetic Measurement System with 39ch SQUIDs Magnetometer for a Three Dimensional Magnetic Measurement" 1998vol. 118,Issue 11,pp. 524-531.
Kensuke Sekihara,"Signal Space Separation Method fora Biomagnetic Sensor Array Arranged on a Flat Plane for Magnetocardiographic Applications:A Computer Simulation Study" Hindawi Journal of Healthcare Engineering vol. 2018, Article ID 7689589, 19 pages.
Samu Taulu et al.,"Presentation of electromagnetic multichannel data: The signal space separation method",Journal of Applied Physics 97, 124905, (2005),pp. 124905-1-10.
Samu Taulu et al.,"Applications of the Signal Space Separation Method", IEEE Transactions on Signal Processing, vol. 53, No. 9, Sep. 2005,pp. 3359-3372.
Koichiro Kobayashi et al."Development of Biomagnetic Measurement System with 39ch SQUIDs Magnetometer for a Three Dimensional Magnetic Measurement" T.IEE Japan, vol. 118 Issue 11,1998, pp. 524-531.
Office Action issued for counterpart U.S. Appl. No. 16/365,689, issued by the US Patent and Trademark Office dated Mar. 7, 2022.
International Search Report and (ISA/237) Written Opinion of the International Search Authority for International Patent Application No. PCT/JP2019/032548, issued/mailed by the Japan Patent Office dated Oct. 21, 2019.
Samu Taula et al.,"Presentation of electromagnetic multichannel data: The signal space separation method", Journal of Applied Physics 97, 124905 (2005),pp. 124905-1-124905-10.
Kensuke Skihara,"Signal Space Separation Method for a Biomagnetic Sensor Array Arranged on a Flat Plane for Magnetocardiographic Applications: A Computer Simulation Study",Journal of Healthcare Engineering vol. 2018, Article ID 7689589, pp. 1-19, https://doi.org/10.1155/2018/7689589.

* cited by examiner

MAGNETIC FIELD MEASUREMENT APPARATUS

The contents of the following Japanese patent application(s) are incorporated herein by reference:
2019-043019 filed in JP on Mar. 8, 2019
2020-006131 filed in JP on Jan. 17, 2020

BACKGROUND

1. Technical Field

The present invention relates to a measurement apparatus.

2. Related Art

Conventionally, a sensor is known that detects a very weak magnetic field of approximately 10 pT, and this sensor is used in a magnetocardiograph that measures magnetocardiographic signals caused by electrical polarization of organs such as the heart, for example, as shown in Patent Documents 1 to 4, for example. Furthermore, in a current sensor using a magnetoresistance effect element, it is known that the effect of an environmental magnetic field is cancelled out using a feedback coil, as shown in Patent Document 5, for example.

Patent Document 1: Japanese Patent Application Publication No. 2000-217798
Patent Document 2: Japanese Patent Application Publication No. 2012-152515
Patent Document 3: U.S. Pat. No. 5,642,045
Patent Document 4: Japanese Patent Application Publication No. 2000-284032
Patent Document 5: US Patent Application Publication No. 2015/0253412

SUMMARY

As an example, a SQUID sensor using the Josephson effect can detect a very weak magnetic field, but this requires high-cost liquid helium, a large-scale magnetic shield room, and the like, and so it is not easy to install an apparatus that includes this sensor. Furthermore, a current sensor using the magnetoresistance effect element is small-scale and has high magnetic sensitivity, but the input/output characteristic thereof has poor linearity. Yet further, due to the fluctuation of the sensitivity error and the sensor characteristics, it is difficult to accurately detect a very weak magnetic field using such a current sensor.

In order to solve the above problems, according to a first aspect of the present invention, provided is a measurement apparatus. The measurement apparatus may comprise a magnetic sensor array that is formed by three-dimensionally arranging a plurality of magnetic sensor cells that each include a magnetic sensor, and is capable of detecting an input magnetic field in three axial directions. The measurement apparatus may comprise a measurement data acquiring section that acquires a plurality of measurement values based on the input magnetic field detected by the magnetic sensor array. The measurement apparatus may comprise a magnetic field calculating section that calculates the input magnetic field based on the plurality of measurement values. The measurement apparatus may comprise an error calculating section that calculates a detection error of the input magnetic field, based on the plurality of measurement values and a calculation result obtained by calculating the input magnetic field. The measurement apparatus may comprise a measurement data selecting section that selects a plurality of measurement values to be used for calculating the input magnetic field by the magnetic field calculating section, from among the plurality of measurement values, based on the detection error.

The error calculating section may calculate the detection error for each of the plurality of measurement values, and the measurement data selecting section may select the plurality of measurement values after excluding a measurement value for which the detection error is outside a predetermined range.

The magnetic field calculating section may recalculate the input magnetic field after the measurement value for which the detection error is outside the predetermined range has been excluded.

The magnetic field calculating section may recalculate the input magnetic field at locations where the plurality of measurement values were measured, based on the plurality of measurement values selected by the measurement data selecting section, and the error calculating section may calculate the detection error based on a detection result of the input magnetic field at the locations where the plurality of measurement values were measured.

The magnetic field calculating section may calculate the input magnetic field at the location where the excluded measurement value was measured, based on a coefficient relating to a calculation result of the input magnetic field calculated from the plurality of measurement values selected by the measurement data selecting section.

Each of the plurality of magnetic sensor cells may further include a magnetic field generating section that applies to the magnetic sensor a feedback magnetic field that reduces the input magnetic field detected by the magnetic sensor and an output section that outputs an output signal corresponding to a current caused to flow by the magnetic field generating section in order to generate the feedback magnetic field.

According to a second aspect of the present invention, provided is a measurement apparatus. The measurement apparatus may comprise a magnetic sensor array that is formed by three-dimensionally arranging a plurality of magnetic sensor cells that each include a magnetic sensor, and is capable of detecting an input magnetic field in three axial directions. The measurement apparatus may comprise a measurement data acquiring section that acquires a plurality of measurement values based on the input magnetic field detected by the magnetic sensor array. The measurement apparatus may comprise a magnetic field calculating section that calculates the input magnetic field based on the plurality of measurement values. The measurement apparatus may comprise an error calculating section that calculates a detection error of the input magnetic field, based on the plurality of measurement values and a calculation result obtained by calculating the input magnetic field. The measurement apparatus may comprise a determining section that determines whether to reset at least one magnetic sensor cell among the plurality of magnetic sensor cells, based on the detection error. Each of the plurality of magnetic sensor cells may include a magnetic sensor; a magnetic field generating section that applies to the magnetic sensor a feedback magnetic field that reduces the input magnetic field detected by the magnetic sensor; an output section that outputs an output signal corresponding to a current caused to flow by the magnetic field generating section in order to generate the feedback magnetic field; and a magnetic resetting section that, when the magnetic sensor cell is to be reset, applies to the magnetic sensor a reset magnetic field that magnetically saturates the magnetic sensor.

The error calculating section may calculate the detection error for each of the plurality of measurement values, and the determining section may make a determination to reset a magnetic sensor cell that includes a magnetic sensor used to acquire a measurement value for which the detection error is outside a predetermined range.

The magnetic field calculating section may recalculate the input magnetic field after the magnetic sensor used to acquire the measurement value for which the detection error is outside the predetermined range has been magnetically reset.

The magnetic resetting section may include a switching section that switches whether a feedback current for generating the feedback magnetic field is supplied to the magnetic field generating section, and may supply a reset current to the magnetic field generating section to cause the magnetic field generating section to generate the reset magnetic field in a state where the magnetic field generating section is not supplied with the feedback current.

The magnetic field calculating section may calculate the input magnetic field in a manner to minimize a square of the detection error.

The magnetic field calculating section may perform signal separation on a spatial distribution of the input magnetic field indicated by the plurality of measurement values, with a signal vector having components that are signals output by the respective magnetic sensors when the magnetic sensor array detects a magnetic field having a spatial distribution of an orthonormal function, serving as a base vector, and the error calculating section may calculate the detection error based on a result obtained by the signal separation performed by the magnetic field calculating section.

The measurement apparatus may further comprise a base vector updating section that updates the base vector based on the detection error.

Each magnetic sensor may include a magnetoresistance effect element.

Each magnetic sensor may further include two magnetic flux concentrators arranged at respective ends of the magnetoresistance effect element, and the magnetoresistance effect element may be arranged at a position sandwiched between the two magnetic flux concentrators.

A coil for generating the feedback magnetic field may be wound to surround the magnetoresistance effect element and the two magnetic flux concentrators.

The measurement apparatus may further comprise a plurality of AD converters that convert outputs of the plurality of magnetic sensor cells from analog to digital, to output the plurality of measurement values, and the plurality of AD converters may perform AD conversion according to a common sampling clock.

A cardiac magnetic field generated by the electrical activity of a heart of an animal may be a measurement target, and the cardiac magnetic field may be measured based on a calculation result of the magnetic field calculating section.

The summary clause does not necessarily describe all necessary features of the embodiments of the present invention. The present invention may also be a sub-combination of the features described above.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
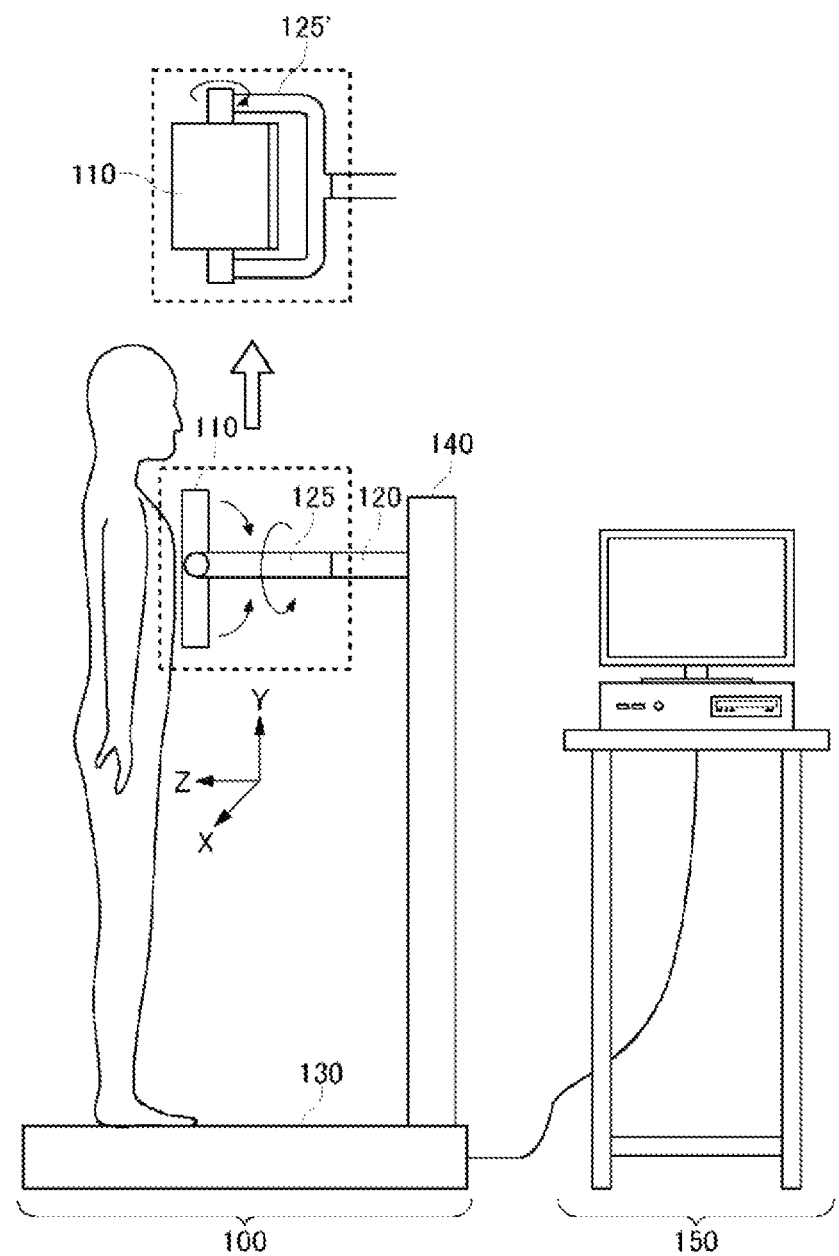
FIG. 1 shows a configuration of a measurement apparatus 10 according to the present embodiment.

FIG. 1 shows a configuration of a measurement apparatus 10 according to the present embodiment. The measurement apparatus 10 measures a magnetic field using a magnetoresistance effect element. The measurement apparatus 10, which is an example of a magnetocardiograph, measures a magnetic field generated by the electrical activity of a human heart (referred to as "cardiac magnetic field"). Instead, the measurement apparatus 10 may be used to measure the cardiac magnetic field of a non-human living creature, or may be used to measure a biomagnetic field other than cardiac magnetic field, such as a brain magnetic field. Furthermore, the measurement apparatus 10 may be used for magnetic flaw inspection to detect scratches on a surface or subsurface of steel materials or welded portions.

The measurement apparatus 10 includes a main body 100 and an information processing section 150. The main body 100 is a component for sensing the cardiac magnetic field of a subject, and includes a magnetic sensor unit 110, a head 120, a driving section 125, a base portion 130, and a pole portion 140.

The magnetic sensor unit 110 is arranged facing the heart in the chest of the subject when measuring the magnetic field, and senses the cardiac magnetic field of the subject. The head 120 supports the magnetic sensor unit 110, and causes the magnetic sensor unit 110 to face the subject. The driving section 125 is provided between the magnetic sensor unit 110 and the head 120, and changes the orientation of the magnetic sensor unit 110 relative to the head 120 when performing calibration. The driving section 125 according to the present embodiment includes a first actuator that can cause the magnetic sensor unit 110 to rotate 360 degrees about a Z-axis in the drawing and a second actuator that causes the magnetic sensor unit 110 to rotate about an axis perpendicular to the Z-axis (an X-axis for the state in the drawing), and changes the azimuth angle and zenith angle of the magnetic sensor unit 110 using these actuators. As shown by the driving section 125 in the drawing, the driving section 125 is Y-shaped when viewed from the Y-axis direction in the drawing, and the second actuator can cause the magnetic sensor unit 110 to rotate 360 degrees about the X-axis in the drawing.

The base portion 130 is a base platform that supports other components, and is a platform the subject steps on during the cardiac magnetic field measurement in the present embodiment. The pole portion 140 supports the head 120 at the height of the chest of the subject. The pole portion 140 may be capable of extending and contracting in an up-down direction in order to adjust the height of the magnetic sensor unit 110 to the height of the chest of the subject.

The information processing section 150 is a component for processing measurement data obtained by the main body 100 and outputting this data through printing, displaying, or the like. The information processing section 150 may be a computer such as a PC (personal computer), a tablet computer, a smartphone, a workstation, a server computer, or a general-purpose computer, or may be a computer system in which a plurality of computers are connected. Instead, the information processing section 150 may be a specialized computer designed for information processing of magnetocardiographic measurement, or may be specialized hardware achieved with a specialized circuit.

Figure 2:
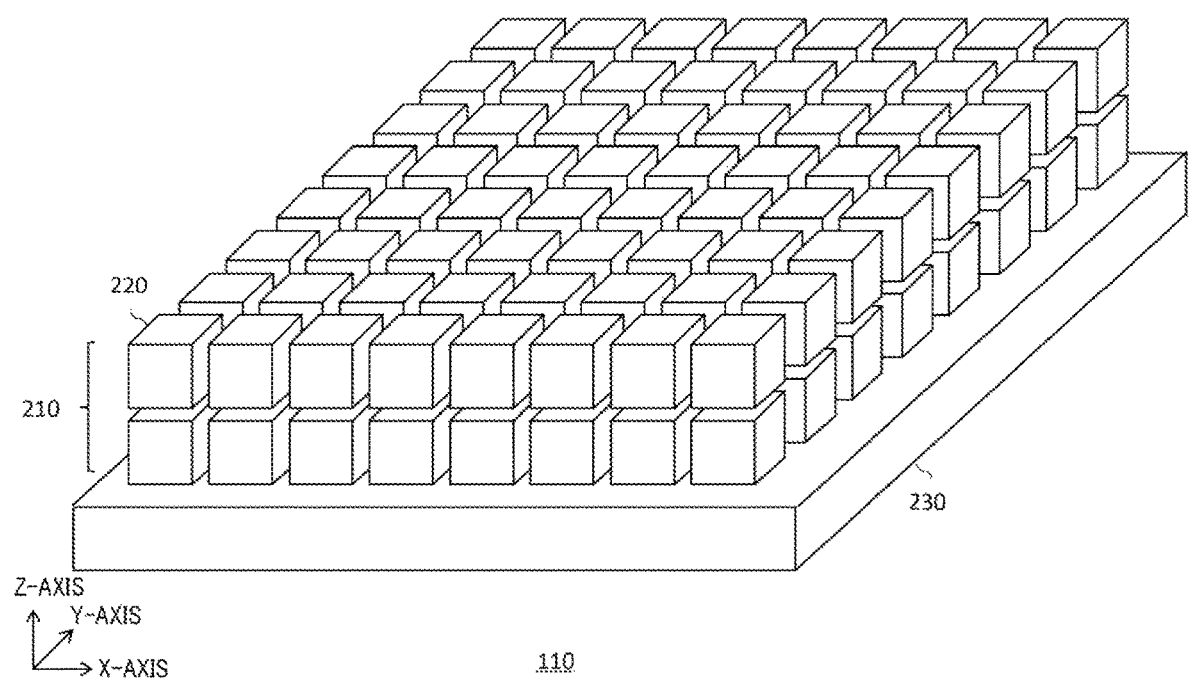
FIG. 2 shows a configuration of the magnetic sensor unit 110 according to the present embodiment.

FIG. 2 shows a configuration of the magnetic sensor unit 110 according to the present embodiment. The magnetic sensor unit 110 includes a magnetic sensor array 210 and a sensor data gathering section 230. The magnetic sensor array 210 is formed by arranging a plurality of magnetic sensor cells 220 three-dimensionally, and is capable of detecting an input magnetic field in three axial directions. In the present drawing, the plurality of magnetic sensor cells 220 in the magnetic sensor array 210 are arranged in a planar shape, in each of the X-direction, the Y-direction, and the Z-direction (e.g. a total of 128 magnetic sensor cells 220 in an arrangement with 8 in the X direction, 8 in the Y direction, and 2 in the Z direction).

The sensor data gathering section 230 is electrically connected to the plurality of magnetic sensor cells 220 included in the magnetic sensor array 210 (not shown in the drawings), gathers sensor data (detection signals) from the plurality of magnetic sensor cells 220, and supplies this sensor data to the information processing section 150.

Figure 3:
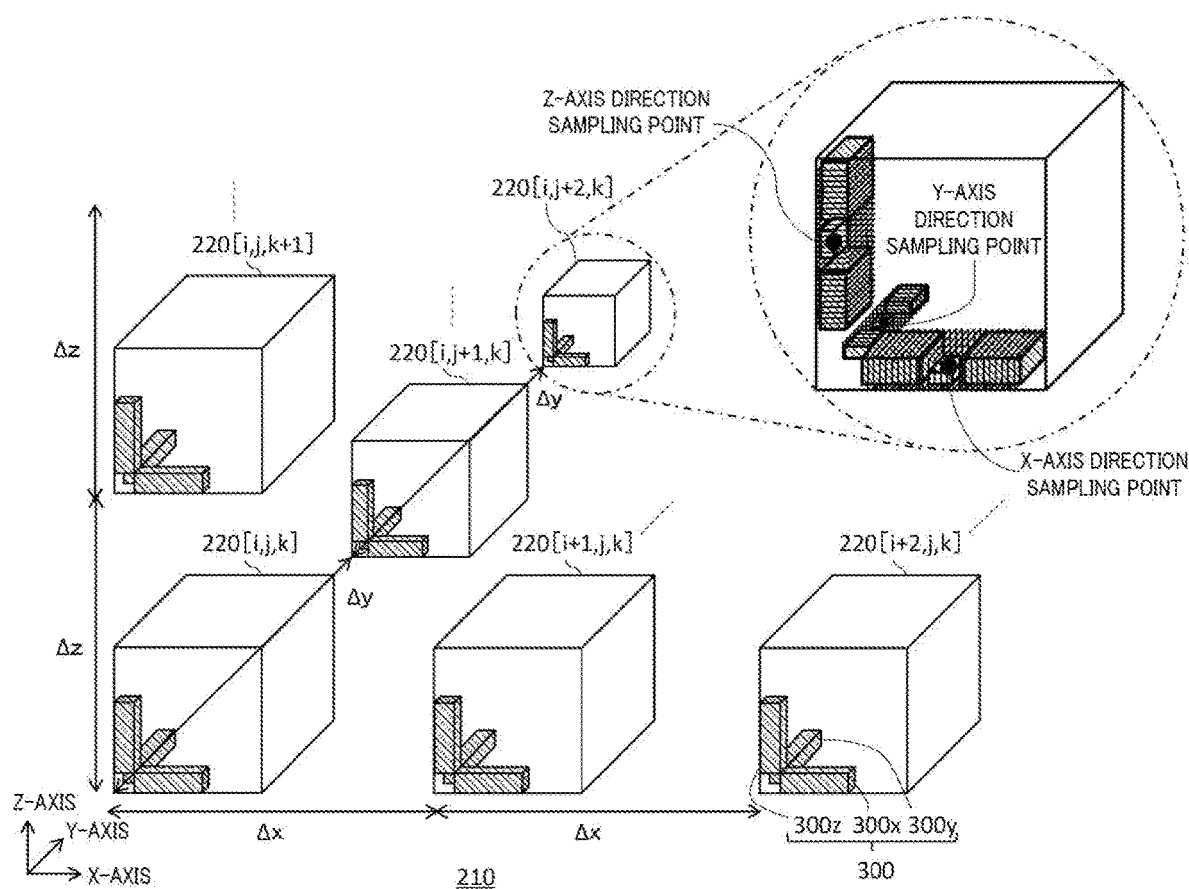
FIG. 3 shows a configuration and arrangement of the magnetic sensor cells 220 in the magnetic sensor array 210 according to the present embodiment.

FIG. 3 shows a configuration and arrangement of the magnetic sensor cells 220 in the magnetic sensor array 210 according to the present embodiment. Each of the plurality of magnetic sensor cells 220 includes at least one sensor section 300, and each sensor section 300 includes a magnetoresistance effect element. In the present drawing, an example is shown of a case in which each of the plurality of magnetic sensor cells 220 includes three sensor sections 300$x$ to 300$z$ (referred to collectively as "sensor sections 300"), and is capable of detecting an input magnetic field in three axial directions. However, not all of the plurality of magnetic sensor cells 220 are limited to including the three sensor sections 300$x$ to 300$z$, and it is only necessary for at least a portion of the magnetic sensor array 210 to be capable of detecting the input magnetic field in three axial directions. The sensor sections 300$x$ are arranged along the X-axis direction and are capable of detecting a magnetic field in the X-axis direction. The sensor sections 300$y$ are arranged along the Y-axis direction and are capable of detecting a magnetic field in the Y-axis direction. The sensor sections 300$z$ are arranged along the Z-axis direction and are capable of detecting a magnetic field in the Z-axis direction. As shown by the magnified view indicated by the single-dot chain line in the present drawing, in the present embodiment, each sensor section 300 includes magnetic flux concentrators arranged at respective ends of each magnetoresistance effect element. Accordingly, each sensor section 300 samples a spatial distribution of a magnetic field using the magnetoresistance effect elements arranged in a narrow region sandwiched by magnetic flux concentrators, thereby making it possible to clarify a sampling point in this space in each axial direction. The details of the configuration of each sensor section 300 are described further below.

In the present drawing, the three axial directions of the magnetic field detected by the sensor sections 300$x$, 300$y$, and 300$z$ are the same as the directions of the three dimensions in which the magnetic sensor cells 220 are arranged. Therefore, it is easy to understand each component of the distribution of the measured magnetic field. It is preferable that, within each magnetic sensor cell 220, the three sensor sections 300$x$, 300$y$, and 300$z$ do not overlap with each other in any of the three dimensional directions in which the magnetic sensor cells 220 are arranged, and one end of each sensor section 300 is provided facing a gap provided between the three sensor sections 300 and the other end of each sensor section 300 is arranged extending away from this gap in the corresponding axial direction among the three axial directions. However, the three axial directions in which the magnetic field is detected may instead be different from the three dimensional directions in which the magnetic sensor cells 220 are arranged. For example, instead of the X-axis, Y-axis, and Z-axis serving as the three axial directions in which the magnetic field is detected, the r-axis, θ-axis, and φ-axis of the polar coordinate system may be used. Furthermore, instead of the X-axis, Y-axis, and Z-axis, the r-axis, θ-axis, and φ-axis of the polar coordinate system may be used as the three dimensional directions in which the magnetic sensor cells 220 are arranged. In a case where the three axial directions in which the magnetic field is detected are different from the three dimensional directions in which the magnetic sensor cells 220 are arranged, there are no restrictions on the arrangement of the sensor sections 300 in the magnetic sensor cells 220 and the arrangement directions of the magnetic sensor cell 220, and it is possible to increase flexibility of the design of the magnetic sensor array 210.

Figure 4:
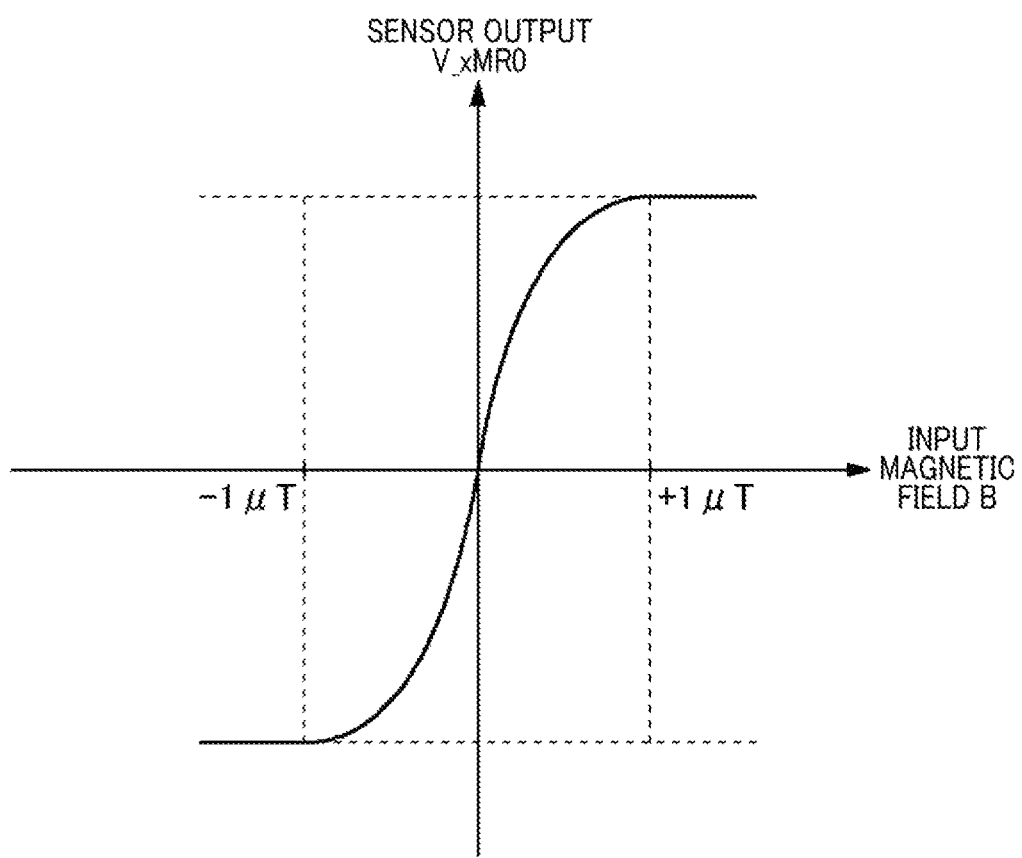
FIG. 4 shows an example of an input/output characteristic of a magnetic sensor including a magnetoresistance effect element according to the present embodiment.

FIG. 4 shows an example of an input/output characteristic of a magnetic sensor including a magnetoresistance effect element according to the present embodiment. In the present drawing, the horizontal axis indicates a magnitude B of an input magnetic field that is input to the magnetic sensor, and the vertical axis indicates a magnitude V_xMR0 of a detection signal of the magnetic sensor. The magnetic sensor includes a GMR (Giant Magneto-Resistance) effect element or a TMR (Tunnel Magneto-Resistance) effect element, for example, and detects the magnitude of the magnetic field in one predetermined axial direction.

Such a magnetic sensor has high magnetic sensitivity, which is the slope of the detection signal V_xMR0 relative to the input magnetic field B, and can detect a very small magnetic field of approximately 10 pT. At the same time, however, the detection signal V_xMR0 becomes saturated when the absolute value of the input magnetic field B is approximately 1 µT, for example, and the magnetic sensor has a narrow range in which the linearity of the input/output characteristic is good. To overcome this, when a closed loop is added to such a magnetic sensor, which generates a feedback magnetic field, it is possible to improve the linearity of the magnetic sensor. The following describes such a magnetic sensor.

Figure 5:
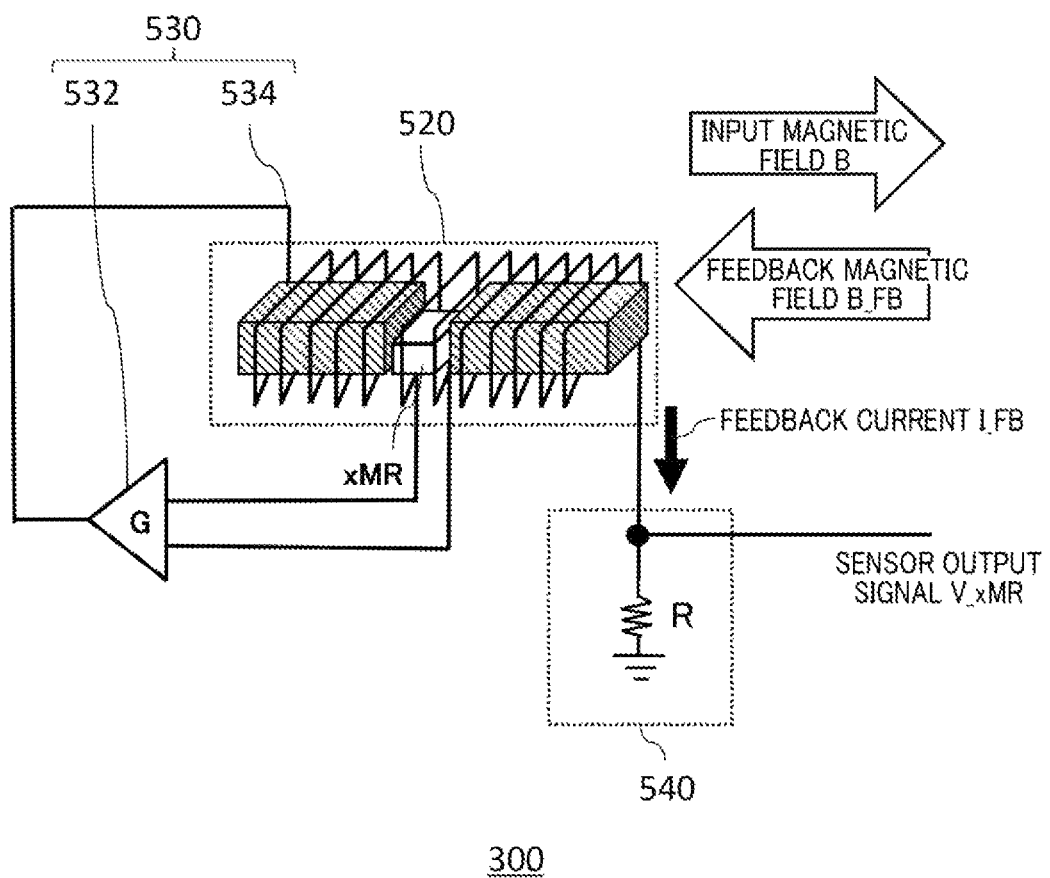
FIG. 5 shows an example of a configuration of a sensor section 300 according to the present embodiment.

FIG. 5 shows an example of a configuration of a sensor section 300 according to the present embodiment. The sensor section 300 is provided inside each of the plurality of magnetic sensor cells 220, and each sensor section 300 includes a magnetic sensor 520, a magnetic field generating section 530, and an output section 540. A portion of the sensor section 300, such as a first amplification circuit 532 and the output section 540, may be provided on the sensor data gathering section 230 side instead of the magnetic sensor cell 220 side.

In the same manner as the magnetic sensor described in FIG. 4, the magnetic sensor 520 includes a magnetoresistance effect element such as a GMR element or TMR element. Furthermore, each magnetic sensor 520 includes a magnetoresistance effect element and two magnetic flux concentrators arranged at respective ends of the magnetoresistance effect element, and the magnetoresistance effect element is arranged at a position sandwiched between the two magnetic flux concentrators. The magnetoresistance effect element of the magnetic sensor 520 may be configured such that, in a case where a positive direction of the magnetosensitive axis is the +X direction, the resistance value of the magnetoresistance effect element increases when a magnetic field of the +X direction is input and decreases when a magnetic field of the −X direction is input. In other words, by measuring a change of the resistance value of the magnetoresistance effect element of the magnetic sensor 520, it is possible to detect the magnitude of the magnetic field B input to this magnetic sensor 520. For example, when the magnetic sensitivity of the magnetic sensor 520 is S, the detection result of the magnetic sensor 520 for the input magnetic field B can be calculated as S×B. As an example, the magnetic sensor 520 is connected to a power source or the like, and outputs a voltage drop corresponding to the change of the resistance value, as a detection result of the input magnetic field. The details of the configuration of the magnetic sensor 520 are described further below.

The magnetic field generating section 530 generates a feedback magnetic field that reduces the input magnetic field detected by the magnetic sensor 520, and that has a magnitude corresponding to the output signal output by the output section 540, and provides this feedback magnetic field to the magnetic sensor 520. For example, the magnetic field generating section 530 operates to cause the generation of a feedback magnetic field B_FB having an orientation that is the opposite of the orientation of the magnetic field B input to the magnetic sensor 520 and an absolute value that is substantially the same as that of the input magnetic field, to cancel out the input magnetic field. The magnetic field generating section 530 includes an amplification circuit 532 and a coil 534.

The amplification circuit 532 outputs a current corresponding to a detection result of the input magnetic field of the magnetic sensor 520, as a feedback current I_FB. In a case where the magnetoresistance effect element of the magnetic sensor 520 is formed by a bridge circuit including at least one magnetoresistance effect element, the outputs of the bridge circuit are connected respectively to a pair of input terminals of the amplification circuit 532. The amplification circuit 532 outputs a current corresponding to the output of the bridge circuit as the feedback current I_FB. The amplification circuit 532 includes a transconductance amplifier, for example, and outputs the feedback current I_FB corresponding to the output voltage of the magnetic sensor 520. For example, when a voltage/current conversion coefficient of the amplification circuit 532 is G, the feedback current I_FB can be calculated as G×S×B.

The coil 534 generates a feedback magnetic field B_FB corresponding to the feedback current I_FB. The coil 534 is wound along an axial direction of the magnetic field that is the detection target of the magnetic sensor 520, in a manner to surround the magnetoresistance effect element of the magnetic sensor 520 and the two magnetic flux concentrators arranged at the respective ends of the magnetoresistance effect element. The coil 534 preferably generates the feedback magnetic field B_FB to be uniform across the entire magnetic sensor 520. For example, when a coil coefficient of the coil 534 is β, the feedback magnetic field B_FB can be calculated as β×I_FB. Here, the feedback magnetic field B_FB is generated with an orientation that cancels out the input magnetic field B, and therefore the magnetic field input to the magnetic sensor 520 is reduced to B−B_FB. Accordingly, the feedback current I_FB is shown by the following expression.

$$I\_FB = G \times S \times (B - \beta \times I\_FB) \qquad \text{Expression 1:}$$

When Expression 1 is solved for the feedback current I_FB, it is possible to calculate the value of the feedback current I_FB in a steady state of the sensor section 300. When the magnetic sensitivity S of the magnetic sensor 520 and the voltage/current conversion coefficient G of the first amplification circuit 532 are sufficiently large, the following expression can be calculated from Expression 1.

$$I\_FB = \frac{G \times S \times B}{1 + G \times S \times \beta} \cong \frac{B}{\beta} \qquad \text{Expression 2}$$

The output section 540 outputs an output signal V_xMR corresponding to the feedback current I_FB that is to flow in order for the magnetic field generating section 530 to generate the feedback magnetic field B_FB. For example, the output section 540 includes a resistance element with a resistance value R, and outputs a voltage drop, caused by the feedback current I_FB flowing through this resistance element, as the output signal V_xMR. In this case, the output signal V_xMR is calculated from Expression 2 as shown in the expression below.

$$V\_xMR = R \times I\_FB = \frac{R \times B}{\beta} \quad \text{Expression 3}$$

As described above, the sensor section 300 generates the feedback magnetic field that reduces the magnetic field input thereto from the outside, and therefore the magnetic field substantially input to the magnetic sensor 520 is reduced. Therefore, even when a magnetoresistance effect element that has the characteristics of being non-linear as shown in FIG. 4 and having a narrow operational magnetic field range is used as the magnetic sensor 520 and the absolute value of the input magnetic field B exceeds 1 µT, for example, the sensor section 300 can prevent the detection signal V_xMR from becoming saturated. The following describes the input/output characteristic of such a sensor section 300.

Figure 6:
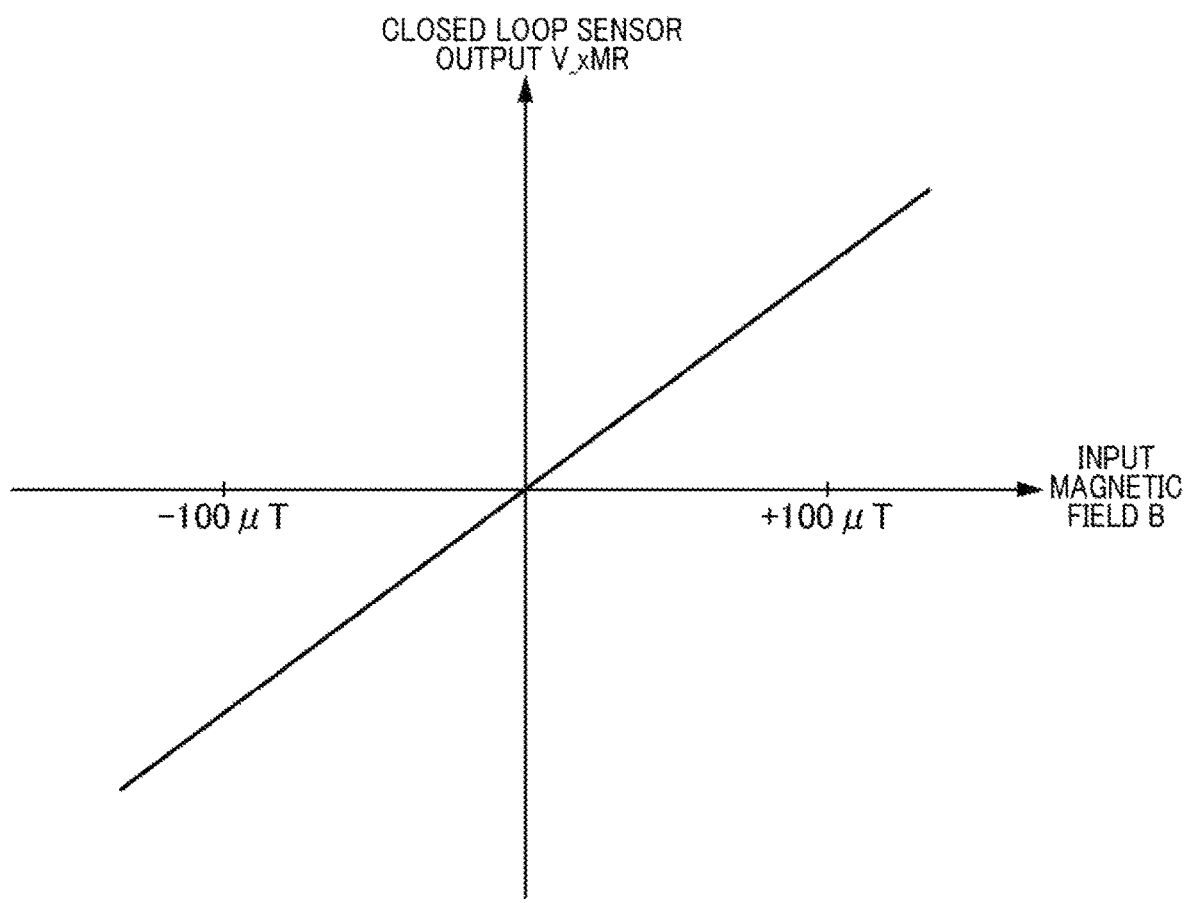
FIG. 6 shows an example of an input/output characteristic of a sensor section 300 according to the present embodiment.

FIG. 6 shows an example of an input/output characteristic of the sensor section 300 according to the present embodiment. In the present drawing, the horizontal axis indicates the magnitude B of the input magnetic field input to the sensor section 300, and the vertical axis indicates the magnitude V_xMR of the detection signal of the sensor section 300. The sensor section 300 has high magnetic sensitivity and can detect a very small magnetic field of approximately 10 pT. Furthermore, even when the absolute value of the input magnetic field B exceeds 100 µT, for example, the sensor section 300 can maintain good linearity for the detection signal V_xMR.

In other words, the sensor section 300 according to the present embodiment is configured such that the detection result for the input magnetic field B is linear in a predetermined range of the input magnetic field B where the absolute value of the input magnetic field B is less than or equal to several hundred µT. By using such a sensor section 300, it is possible to easily detect very weak magnetic signals, such as cardiac magnetic field signals.

Figure 7:
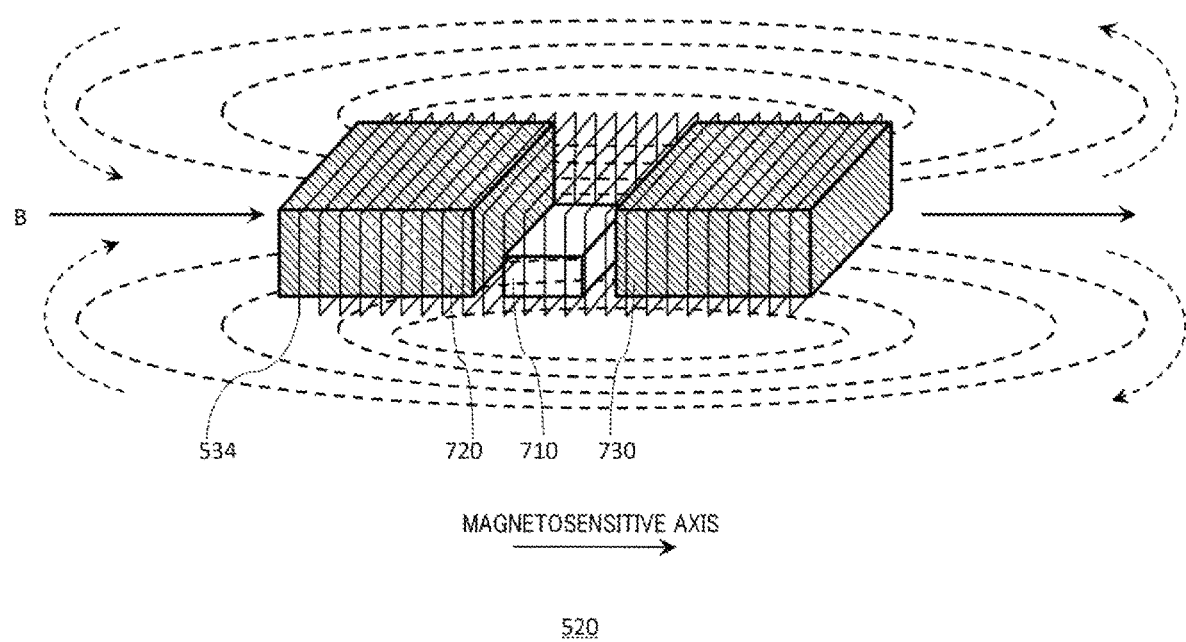
FIG. 7 shows an example of a configuration of a magnetic sensor 520 according to the present embodiment.

FIG. 7 shows an example of a configuration of a magnetic sensor 520 according to the present embodiment. In the present drawing, the magnetic sensor 520 includes a magnetoresistance effect element 710 and magnetic flux concentrators 720 and 730 arranged at the respective ends of the magnetoresistance effect element 710. The magnetic flux concentrators 720 and 730 are arranged at the respective ends of the magnetoresistance effect element 710 in a manner to sandwich the magnetoresistance effect element 710 therebetween. In the present drawing, the magnetic flux concentrator 720 is provided on the negative side of the magnetoresistance effect element 710 along the magnetosensitive axis, and the magnetic flux concentrator 730 is provided on the positive side of the magnetoresistance effect element 710 along the magnetosensitive axis. Here, the magnetosensitive axis may be oriented along a fixed magnetization direction in a fixed-magnetization layer forming the magnetoresistance effect element 710. Furthermore, when a magnetic field is input from the negative side toward the positive side of the magnetosensitive axis, the resistance of the magnetoresistance effect element 710 may increase or decrease. The magnetic flux concentrators 720 and 730 are formed of a material with high permeability such as permalloy, for example. In a case where the magnetic sensor 520 is configured such as shown in the present drawing, the coil 534 is wound along the axial direction of the magnetic field that is the detection target of the magnetic sensor 520, in a manner to surround a cross section of the magnetoresistance effect element 710 and the magnetic flux concentrators 720 and 730 arranged at the respective ends of the magnetoresistance effect element 710. Furthermore, in a case where a plurality of magnetoresistance effect elements 710 are included in one magnetic sensor 520, the magnetic sensor 520 may include a plurality of sets that each include a magnetoresistance effect element and magnetic flux concentrators arranged at the respective ends thereof. In this case, the coils 534 may be wound such that each set including the magnetoresistance effect element and the magnetic flux concentrators arranged at the respective ends thereof is surrounded by one coil.

In such a magnetic sensor 520, when a magnetic field is input from the negative side to the positive side of the magnetosensitive axis, the magnetic flux concentrators 720 and 730 formed of the material with high permeability are magnetized, thereby generating a magnetic field distribution such as shown by the dashed line in the present drawing. When this occurs, the magnetic flux generated by the magnetization of the magnetic flux concentrators 720 and 730 passes through the position of the magnetoresistance effect element 710 sandwiched between the two magnetic flux concentrators 720 and 730. Therefore, the magnetic flux density at the position of the magnetoresistance effect element 710 can be significantly increased by providing the magnetic flux concentrators 720 and 730. Furthermore, it is possible to clarify the sampling point in space by sampling the spatial distribution of the magnetic field using the magnetoresistance effect element 710 arranged in the narrow region sandwiched by the magnetic flux concentrators 720 and 730 as shown in the present drawing.

Figure 8:
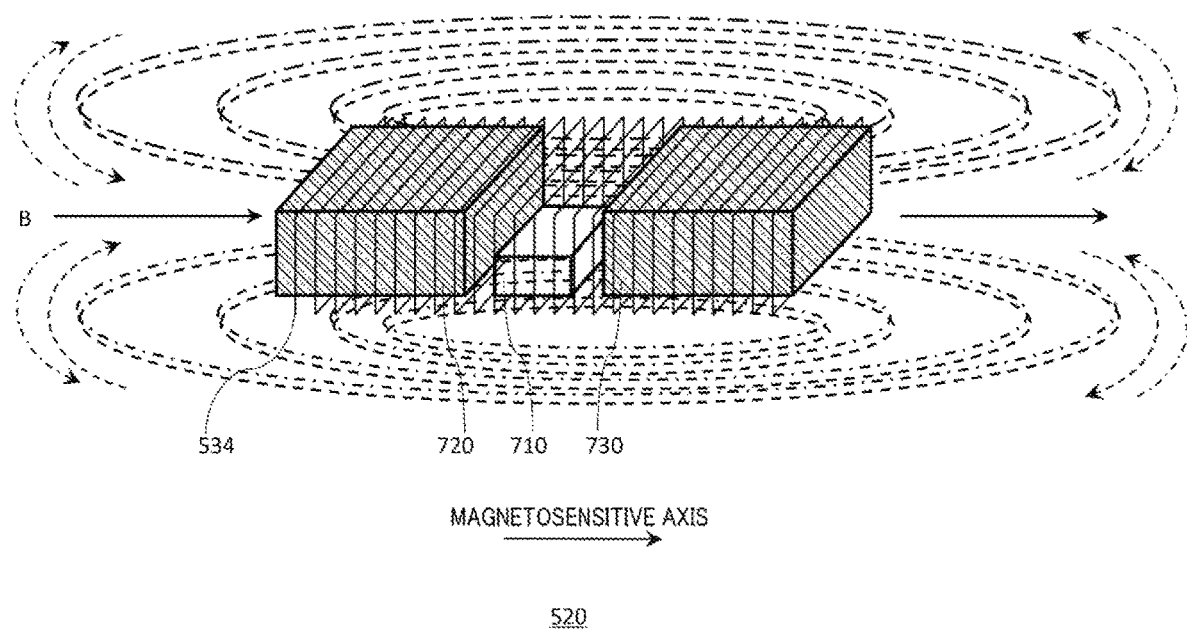
FIG. 8 shows a magnetic flux distribution at a time when the feedback magnetic field has been generated at the magnetic sensor 520 according to the present embodiment.

FIG. 8 shows a magnetic flux distribution at a time when the feedback magnetic field has been generated at the magnetic sensor 520 according to the present embodiment. In FIG. 8, components having the same function and configuration as in FIG. 7 are given the same reference numerals, and the following describes only differing points. In the magnetic sensor 520 according to the present embodiment, when the feedback current is supplied to the coil 534, the coil 534 generates the feedback magnetic field, thereby generating a magnetic flux distribution such as shown by the single-dot chain line in the present drawing. The magnetic flux generated by this feedback magnetic field has a spatial distribution that cancels out the spatial distribution of the magnetic field that has been input to the magnetoresistance effect element 710 and magnetically amplified by the magnetic flux concentrators 720 and 730. Therefore, in a case where the magnetic flux concentrators 720 and 730 are arranged at the respective ends of the magnetoresistance effect element 710 as shown in the present drawings and the coil 534 is wound such that one coil surrounds a set including the magnetoresistance effect element and the magnetic flux concentrators arranged at the respective ends thereof, the magnetic sensor 520 can accurately cancel out the magnetic field distribution at the position of the magnetoresistance effect element 710 with the feedback magnetic field, and therefore it is possible to realize a sensor with high linearity between the input magnetic field and the output voltage.

Figure 9:
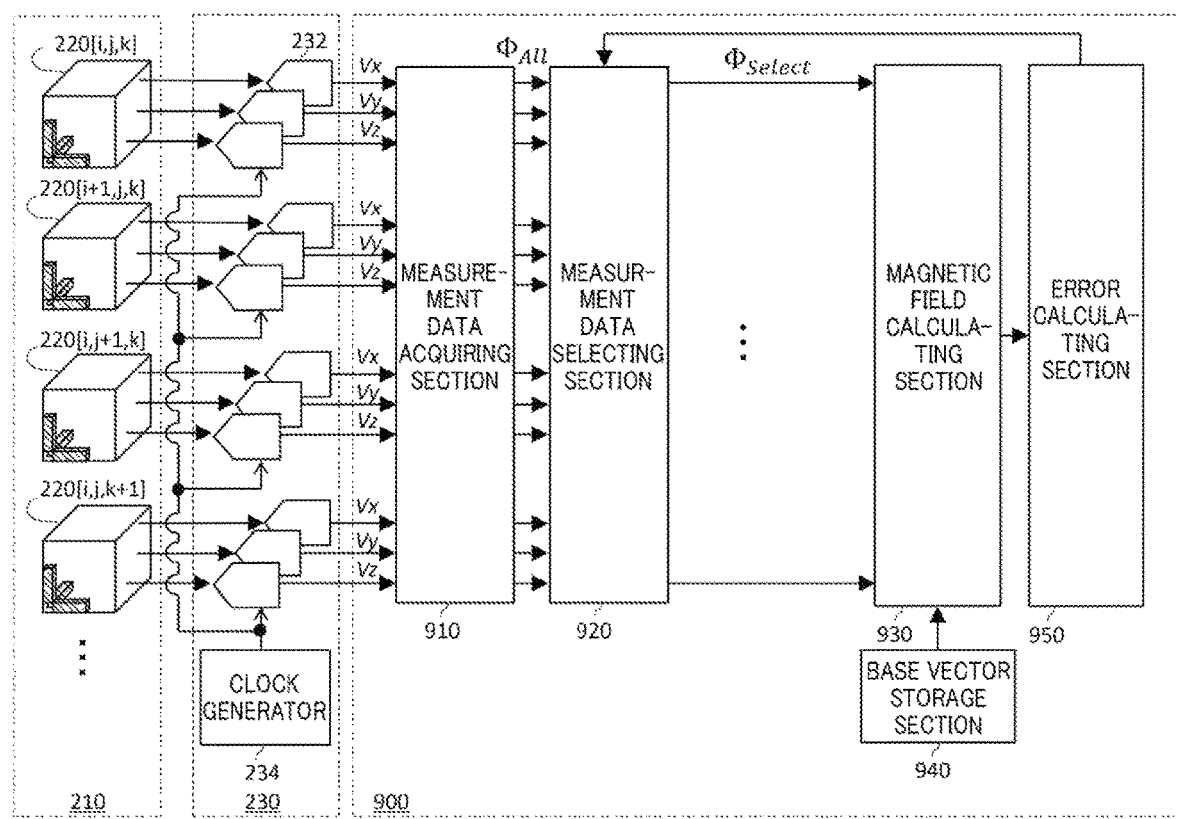
FIG. 9 shows a configuration of a magnetic sensor array 210, a sensor data gathering section 230, and a sensor data processing section 900 according to the present embodiment.

FIG. 9 shows a configuration of a magnetic sensor array 210, a sensor data gathering section 230, and a sensor data processing section 900 according to the present embodiment.

The magnetic sensor array 210 includes a plurality of the magnetic sensor cells 220. Each of the plurality of magnetic sensor cells 220 may include a plurality of sensor sections 300x to 300z, as described above. In the present drawing, among the plurality of magnetic sensor cells 220 included in the magnetic sensor array 210 in each dimensional direction, the portions relating to the positions [i, j, k], [i+1, j, k], [i, j+1, k], and [i, j, k+1] are shown.

The sensor data gathering section 230 includes a plurality of AD converters 232 and a clock generator 234. The plurality of AD converters 232 are provided corresponding respectively to the plurality of sensor sections 300x to 300z of each magnetic sensor cell 220, convert an analog detection signal (the sensor output signal V_xMR of FIG. 6) output by the corresponding sensor section 300 into digital measurement values V (Vx, Vy, Vz), and output the plurality of measurement values. Here, Vx, Vy, and Vz are measurement values (e.g. digital voltage values) obtained by converting the detection signals respectively from the sensor sections 300x, 300y, and 300z into digital signals.

The clock generator 234 generates a sampling clock and supplies a common sampling clock to each of the plurality of AD converters 232. Each of the plurality of AD converters 232 performs an AD conversion according to the common sampling clock supplied from the clock generator 234. Accordingly, all of the plurality of AD converters 232 that perform AD conversions respectively on the outputs of the plurality of sensor sections 300x to 300z provided at different positions operate in synchronization. Therefore, the plurality of AD converters 232 can simultaneously sample the detection results of the plurality of sensor sections 300x to 300z provided in different spatial positions.

The sensor data processing section 900 includes a measurement data acquiring section 910, a measurement data selecting section 920, a magnetic field calculating section 930, a base vector storage section 940, and an error calculating section 950.

The measurement data acquiring section 910 acquires the plurality of measurement values that are based on the input magnetic field detected by the magnetic sensor array 210. The measurement data acquiring section 910 is connected to the plurality of AD converters 232, and acquires the plurality of measurement values measured by the sensor sections 300x to 300z inside the plurality of magnetic sensor cells 220 forming the magnetic sensor array 210. Specifically, the measurement data acquiring section 910 may be formed using flip-flops or the like that latch, at a prescribed timing T, the measurement values V (Vx, Vy, Vz) that have been converted into digital values by the plurality of AD converters 232. The measurement data acquiring section 910 supplies the measurement data selecting section 920 with the acquired plurality of measurement values, as measurement data $\Phi_{All}$.

The measurement data selecting section 920 selects a plurality of measurement values to be used by the magnetic field calculating section 930 to calculate the input magnetic field, from among the plurality of measurement values supplied from the measurement data acquiring section 910, based on a magnetic field detection error described further below. The measurement data selecting section 920 supplies the magnetic field calculating section 930 with the selected plurality of measurement values, as measurement data $\Phi_{Select}$.

The magnetic field calculating section 930 calculates the input magnetic field based on the plurality of measurement values selected by the measurement data selecting section 920 as the measurement data $\Phi_{Select}$. In a case where the cardiac magnetic field generated by the electrical activity of the heart of an animal is the measurement target, the cardiac magnetic field may be measured based on the calculation result of the magnetic field calculating section 930. In this case, the magnetic field calculating section 930 may calculate the input magnetic field in a manner to minimize the square of the detection error of the magnetic field. Furthermore, the magnetic field calculating section 930 may perform signal separation on the spatial distribution of the input magnetic field indicated by the plurality of measurement values, with a signal vector whose components are signals output from respective magnetic sensors 520, when a magnetic field having a spatial distribution of an orthonormal function is detected by the magnetic sensor array 210, serving as a base vector. This signal separation is described further below. The magnetic field calculating section 930 supplies the error calculating section 950 with the calculation results obtained by calculating the input magnetic field and the plurality of measurement values.

The base vector storage section 940 stores the base vector to be used when the magnetic field calculating section 930 performs signal separation on the spatial distribution of the input magnetic field, and supplies the magnetic field calculating section 930 with the stored base vector. The magnetic field calculating section 930 may use the base vector supplied from the base vector storage section 940, when performing signal separation on the spatial distribution of the input magnetic field.

The error calculating section 950 calculates a detection error ε of the magnetic field, based on the plurality of measurement results and the calculation result obtained by calculating the input magnetic field supplied from the magnetic field calculating section 930. This calculation is also described further below. The error calculating section 950 supplies the measurement data selecting section 920 with the calculated detection error ε of the magnetic field. As described above, the measurement data selecting section 920 selects a plurality of measurement values to be used by the magnetic field calculating section 930 to calculate the input magnetic field, from among the plurality of measurement values supplied from the measurement data acquiring section 910, based on the detection error ε of the magnetic field supplied from the error calculating section 950.

Figure 10:
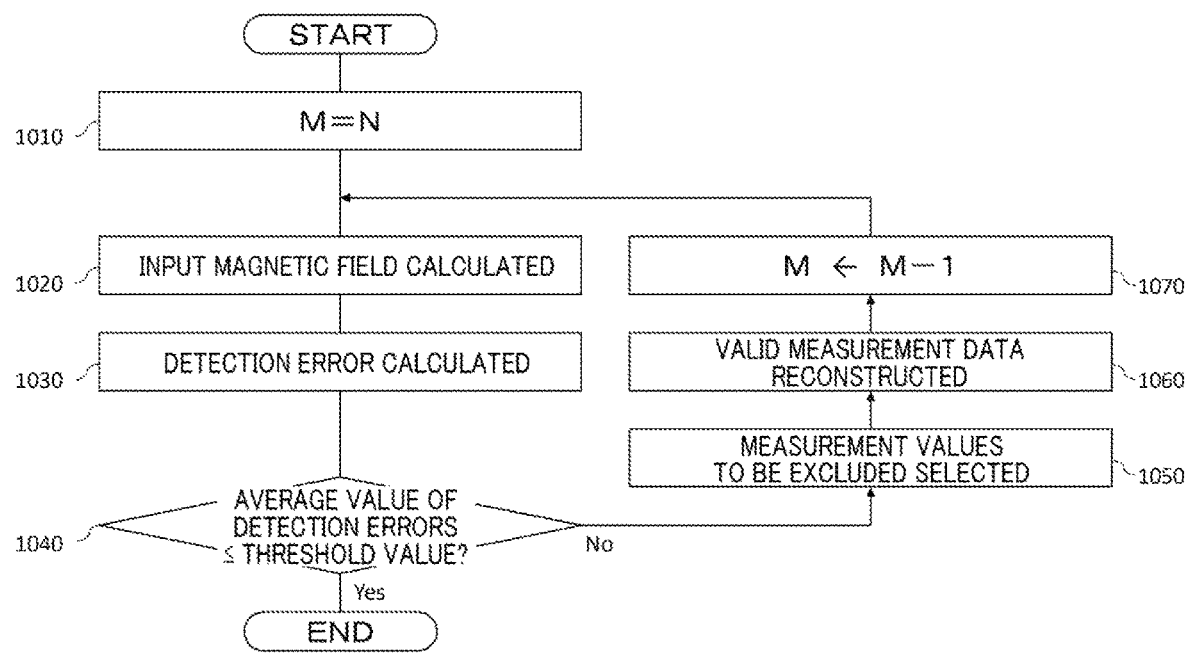
FIG. 10 shows an example of a procedure for excluding measurement values caused by defective sensors, as preprocessing for detecting the measurement target magnetic field with the measurement apparatus 10 according to the present embodiment.

FIG. 10 shows an example of a procedure for excluding measurement values caused by defective sensors, as preprocessing for calculating the measurement target magnetic field with the measurement apparatus 10 according to the present embodiment.

At step 1010, the measurement apparatus 10 performs an initial setting. For example, with N being the total number of the plurality of sensor sections 300x to 300z in the plurality of magnetic sensor cells 220 forming the magnetic sensor array 210, that is, the total number of the plurality of measurement values included in the measurement data $\Phi_{All}$, and M being the total number of the plurality of measurement values included in the measurement data $\Phi_{Select}$, the measurement apparatus 10 sets M=N. In other words, the measurement apparatus 10 performs an initial setting such that all of the plurality of measurement values are the measurement data $\Phi_{Select}$.

Next, at step 1020, the measurement apparatus 10 calculates the input magnetic field. For example, the measurement data acquiring section 910 acquires the plurality of measurement values (measurement data $\Phi_{All}$) that are based on the input magnetic field measured by the sensor sections 300x to 300z in the plurality of magnetic sensor cells 220 forming the magnetic sensor array 210. Then, at step 1020 that follows step 1010, the measurement data selecting section 920 selects all of the plurality of measurement values as the measurement data $\Phi_{Select}$ ($\Phi_{Select}=\Phi_{All}$).

The magnetic field calculating section 930 then calculates the input magnetic field, based on the plurality of measurement values selected as the measurement data $\Phi_{Select}$.

When calculating the input magnetic field, the magnetic field calculating section 930 performs signal separation on the spatial distribution of the input magnetic field indicated by the plurality of measurement values, with a signal vector whose components are signals output from respective magnetic sensors 520, when a magnetic field having a spatial distribution of an orthonormal function is detected by the magnetic sensor array 210, serving as a base vector, for example. The orthonormal function may be a spherical harmonic function, for example. As an example, before the calculation of the measurement target magnetic field, the base vector storage section 940 stores, as the base vector, a magnetic field signal vector obtained by spatially sampling the spherical harmonic function when a predetermined point in space has been designated as a coordinate origin. Here, the spherical harmonic function is a function obtained by restricting, to a unit sphere, the homogeneous polynomial that is a solution to an n-dimensional Laplace equation, and is orthonormal on the sphere. The base vector storage section 940 may store, as the base vector, a signal vector determined in advance by a simulation result or the like.

The magnetic field calculating section 930 acquires this signal vector stored by the base vector storage section 940 as the base vector, from the base vector storage section 940. The magnetic field calculating section 930 performs a series expansion on the spatial distribution of the input magnetic field indicated by the plurality of measurement values, using this signal vector as the base vector. The magnetic field calculating section 930 performs signal separation to separate the spatial distribution of the magnetic field into a measurement target magnetic field and a disturbance magnetic field, using the vector obtained by the series expansion.

The magnetic field calculating section 930 suppresses the disturbance magnetic field and calculates and outputs only the measurement target magnetic field, as the result of the signal separation. The following is a detailed description of this process using expressions.

Concerning the position where each sensor forming the magnetic sensor array 210 is arranged, when the current $i(r)=0$ at a position of a position vector r representing a position from the coordinate origin, the static magnetic field B(r) is obtained as a spatial gradient of a potential V(r), as shown in the expression below, using a potential V(r) that satisfies the Laplace equation $\Delta \cdot V(r)=0$. Here, $\Delta$ is a Laplacian, $\mu$ is the permeability, and $\nabla$ is an operator representing a vector differentiation operation.

$$B(r)=-\mu \cdot \nabla \cdot V(r) \qquad \text{Expression 4:}$$

Since the solution of the Laplace equation is usually in the form of a series expansion using the spherical harmonic function Y1, m($\theta$, $\varphi$), which is an orthonormal function system, the potential V(r) can be expressed as shown in the expression below. Here, |r| is the absolute value of the position vector r (distance from the coordinate origin), $\theta$ and $\varphi$ are two declinations in spherical coordinates, 1 is an azimuthal quantum number, m is a magnetic quantum number, $\alpha$ and $\beta$ are multipole moments, and Lin and Lout are the numbers of series in a space in front of the magnetic sensor array 210 and a space behind the magnetic sensor array 210 when viewed from the coordinate origin and the measurement target, respectively. The azimuthal quantum number 1 is a positive integer, and the magnetic quantum number m is an integer from 1 to +1. In other words, when 1 is 1, for example, m is −1, 0, and 1, and when 1 is 2, for example, m is −2, −1, 0, 1, and 2. Since there is no case of a single magnetic pole in the magnetic field, the azimuthal quantum number 1 starts from 1 instead of 0 in Expression 5. The first term in Expression 5 is a term that is inversely proportional to the distance from the coordinate origin, and indicates the potential in the space in front of the magnetic sensor array 210 viewed from the coordinate origin and the measurement target. Furthermore, the second term in Expression 5 is a term that is proportional to the distance from the coordinate origin, and indicates the potential in the space behind the magnetic sensor array 210 viewed from the coordinate origin and the measurement target.

$$V(r) = \sum_{l=1}^{Lin} \sum_{m=-l}^{l} \alpha_{l,m} \cdot \left( \frac{1}{|r|^{l+1}} \cdot Y_{l,m}(\theta, \phi) \right) + \sum_{l=1}^{Lout} \sum_{m=-l}^{l} \beta_{l,m} \cdot \left( |r|^{l} \cdot Y_{l,m}(\theta, \phi) \right) \qquad \text{Expression 5}$$

Therefore, according to Expression 4 and Expression 5, the static magnetic field B(r) can be expressed by the expression below. Here, the first term in Expression 6 indicates a magnetic field source in the space in front of the magnetic sensor array 210 viewed from the coordinate origin and the measurement target, e.g. the cardiac magnetic field (measurement target magnetic field) created by the electrical activity of the heart. Furthermore, the second term in Expression 6 indicates the disturbance magnetic field created by a magnetic field source behind the magnetic sensor array 210 viewed from the coordinate origin and the measurement target.

$$B(r) = -\mu \sum_{l=1}^{Lin} \sum_{m=-l}^{l} \alpha_{l,m} \cdot \nabla \left( \frac{1}{|r|^{l+1}} \cdot Y_{l,m}(\theta, \phi) \right) - \mu \sum_{l=1}^{Lout} \sum_{m=-l}^{l} \beta_{l,m} \cdot \nabla \left( |r|^{l} \cdot Y_{l,m}(\theta, \phi) \right) \qquad \text{Expression 6}$$

In a case where the solution of the Laplace equation is expressed in the form a series expansion using a spherical harmonic function, this general solution is an infinite series, but, for example, it is only necessary to be able to obtain an SNR (signal-to-noise ratio, that is, a ratio of the measurement target magnetic field signal to the disturbance magnetic field and sensor noise) sufficient for measuring a biomagnetic field, and it is said that a series expressed by 10 terms is actually sufficient. Furthermore, it is said that approximately Lin=8 and Lout=3 is sufficient for a series of signal space separations in magnetoencephalography. Accordingly, an example of a case in which Lin=8 and Lout=3 is described for the measurement apparatus 10 according to the present embodiment as well, which may be used as a magnetocardiograph, for example. However, the Lin and Lout values are not limited to this, and may be any numerical values that are sufficient for sufficiently suppressing the disturbance magnetic field and calculating the measurement target magnetic field.

Here, K is defined as a calibration coefficient matrix expressing the error of each sensor included in the magnetic sensor array 210, and a1, m and b1, m are defined as shown in the following expression. Essentially, assume a1, m and b1, m to be base vectors for which the magnetic sensitivity error of the magnetic sensor array 210 has been corrected, obtained by multiplying the calibration coefficient matrix K for correcting the magnetic sensitivity error of the magnetic sensor 520 included in the magnetic sensor array 210 by an M-dimensional vector having M components, where M is equal to the number of sensors included in the magnetic sensor array 210, obtained from the gradient of the spherical harmonic function Y1, m(θ, φ).

$$a_{l,m} = K \cdot \left[ -\mu \nabla \left( \frac{1}{|r|^{l+1}} \cdot Y_{l,m}(\theta, \phi) \right) \right]$$

$$b_{l,m} = K \cdot \left[ -\mu \nabla \left( |r|^{l} \cdot Y_{l,m}(\theta, \phi) \right) \right]$$

Expression 7

In this case, the measurement data $\Phi_{Select}$ at a certain timing can be expressed as shown in the expression below.

$$\Phi_{Select} = \sum_{l=1}^{Lin} \sum_{m=-l}^{l} \alpha_{l,m} \cdot a_{l,m} + \sum_{l=1}^{Lout} \sum_{m=-l}^{l} \beta_{l,m} \cdot b_{l,m}$$

Expression 8

Furthermore, Sin, Sout, Xin, and Xout are each defined in the following manner. Essentially, Sin is defined as vector of total Lin·(Lin+2) column in which each vector a at each integer timing of l, from m=−1 to m=1, is arranged in series order from l=1 to l=Lin. Furthermore, Sout is defined as vector of total Lout·(Lout+2) column in which each vector b at each integer timing of l, from m=−1 to m=1, is arranged in series in order from l=1 to l=Lout. Yet further, Xin is defined as a vector of total Lin·(Lin+2) row obtained by transposing a vector in which each multipole moment a at each integer timing of l, from m=−1 to m=1, is arranged in series order from l=1 to l=Lin. Yet further, Xout is defined as a vector of total Lout·(Lout+2) row obtained by transposing a vector in which each multipole moment β at each integer timing of l, from m=−1 to m=1, is arranged in series order from l=1 to l=Lout.

$$Sin=[a_{1,-1}a_{1,0}a_{1,+1} \ldots a_{Lin,Lin}]$$

$$Sout=[b_{1,-1}b_{1,0}b_{1,+1} \ldots b_{Lout,Lout}]$$

$$xin=[\alpha_{1,-1}\alpha_{1,0}\alpha_{1,+1} \ldots \alpha_{Lin,Lin}]^t$$

$$xout=[\beta_{1,-1}\beta_{1,0}\beta_{1,+1} \ldots \beta_{Lout,Lout}]^t$$

Expression 9

In this case, the valid measurement data $\Phi_{Select}$ can be expressed as the dot product of a matrix S and a vertical vector X. Here, the matrix S indicates a matrix obtained by arranging a number, equal to total Lin·(Lin+2)+total Lout·(Lout+2), of base vectors in the horizontal direction, e.g. a matrix acquired from the base vector storage section 940 by the magnetic field calculating section 930. Furthermore, the (Lin·(Lin+2)+total Lout·(Lout+2)–dimensional vertical vector X indicates a coefficient of linear combination of the base vectors.

$$\Phi_{Select} = S \cdot X = [Sin, Sout] \cdot \begin{bmatrix} Xin \\ Xout \end{bmatrix}$$

Expression 10

The magnetic field calculating section 930 determines a vertical vector ^X (Here, ^X indicates the left side in Expression 11, and means the hat (estimated value) of X) using the following expression, based on the model expression of the measurement data $\Phi_{Select}$ obtained from Expression 10.

$$\hat{X} = \begin{bmatrix} \widehat{Xin} \\ \widehat{Xout} \end{bmatrix} = (S^t \cdot S)^{-1} \cdot S^t \cdot \Phi_{Select}$$

Expression 11

At this time, the magnetic field calculating section 930 determines the vertical vector ^X in a manner to minimize a cost function F shown by the expression below, using the least squares technique. In this way, the magnetic field calculating section 930 can solve for the spatial distribution of the magnetic field.

$$F=|\Phi_{Select}-S\cdot\hat{X}|^2$$

Expression 12:

Here, concerning the vertical vector ^X determined by the magnetic field calculating section 930 using Expression 11 and Expression 12, Sin·^Xin represents the measurement target magnetic field component (cardiac magnetic field) and Sout·^Xout represents the disturbance magnetic field component. Therefore, in order to eliminate the disturbance magnetic field component and extract only the measurement target magnetic field component, it is only necessary to extract Sin·^Xin from the magnetic field detection result S·^X.

Due to this, the magnetic field calculating section 930 can perform signal separation on the spatial distribution of the magnetic field indicated by the measurement data $\Phi_{Select}$ measured by the magnetic sensor array 210 that is formed by three-dimensionally arranging the plurality of magnetic sensor cells 220 and is capable of detecting the input magnetic field into three axial direction, to separate this spatial distribution into the measurement target magnetic field and the disturbance magnetic field. In this way, the measurement apparatus 10 can suppress the disturbance magnetic field component and extract only the measurement target magnetic field component, and can therefore measure the measurement target magnetic field with higher accuracy. Furthermore, since the plurality of sensor sections 300 each include magnetic flux concentrators, it is possible to increase the magnetic sensitivity of the sensor sections 300, clarify the sampling points in space, and increase the affinity with signal space separation technology. The magnetic field calculating section 930 supplies the error calculating section 950 with the calculation result obtained by calculating the input magnetic field, along with the plurality of measurement values.

At step 1030, the error calculating section 950 calculates the detection error ε of the magnetic field, based on the calculation result obtained by calculating the input magnetic field and the plurality of measurement values supplied from the magnetic field calculating section 930. For example, the error calculating section 950 may calculate the detection error ε by subtracting the dot product of the matrix S and the vertical vector ^X from the measurement data $\Phi_{Select}$, as shown in the expression below. In this way, the error calculating section 950 calculates, for each vector component, the error occurring when the measurement data $\Phi_{Select}$ at a certain timing was mapped to a partial space spanned by the base vector S=[Sin, Sout] using the least squares technique, and sets this error as the detection error ε. Accordingly, the error calculating section 950 calculates a detection error ε for each of the plurality of measurement values. The error calculating section 950 supplies the measurement data selecting section 920 with the calculated detection errors ε of the magnetic field. Since the number of measurement values is M, the detection error ε is a vertical vector having M rows.

$$\varepsilon = \Phi_{Select} - S \cdot \hat{X} \qquad \text{Expression 13:}$$

At step 1040, the measurement data selecting section 920 judges whether the average value of the detection errors c in the entire magnetic sensor array 210, that is the average value of the detection errors c of every one of the plurality of measurement values, is less than or equal to a predetermined threshold value. For example, the measurement data selecting section 920 may calculate an average value avg(ε) of the detection errors c according to the expression shown below, and judge whether the average value avg(ε) of the detection errors c is less than or equal to the predetermined threshold value Avg_E_Th.

$$avg(\varepsilon) = \sqrt{\sum_{m=1}^{M} \varepsilon(m)^2 / M} \qquad \text{Expression 14}$$

At step 1040, if it is judged that the average value of the detection errors c is less than or equal to the predetermined threshold value, the measurement apparatus 10 ends the process of the procedure for excluding measurement values caused by defective sensors.

On the other hand, at step 1040, if it is judged that the average value of the detection errors c exceeds the predetermined threshold value, at step 1050, the measurement data selecting section 920 selects measurement values for which the detection error ε is outside a predetermined range, from among the plurality of measurement values, as measurement values to be excluded. As an example, the measurement data selecting section 920 may select a measurement value i having the largest absolute value for the detection error ε, in the magnetic sensor array 210, as a measurement value to be excluded.

Next, at step 1060, the measurement data selecting section 920 selects a plurality of measurement values after excluding the measurement value i for which the detection error ε is outside the predetermined range. In other words, the measurement data selecting section 920 reconstructs the measurement data $\Phi_{Select}$ to include only the plurality of measurement values excluding the measurement value i.

At step 1070, as a result of having excluded the measurement value i, the measurement data selecting section 920 decrements the order of M by 1 and the process returns to step 1020. Then, after the measurement value i for which the detection error is outside the predetermined range has been excluded, at step 1020, the magnetic field calculating section 930 recalculates the input magnetic field. At this time, the magnetic field calculating section 930 may newly reacquire measurement values using the magnetic sensor array 210, or may reuse the measurement values that have already been acquired. At step 1040, the measurement apparatus 10 repeats this process until it is judged that the average value of the detection errors c is less than or equal to the predetermined threshold value.

The above describes an example of a case in which, when it is judged that the average value of the detection errors c exceeds the predetermined threshold value, the measurement apparatus 10 excludes one measurement value i for which the absolute value of the detection error ε is relatively the largest, and repeats this procedure. However, the present embodiment is not limited to this. The measurement apparatus 10 may first select one measurement value i for which the absolute value of the detection error ε is relatively the largest and then, if it is judged that the detection error for this measurement value i, i.e. the largest absolute value of a detection error ε, exceeds the predetermined threshold value, exclude this measurement value i and repeat the procedure. Furthermore, the measurement apparatus 10 may select a plurality of valid measurement values after excluding one or more measurement values i for which the absolute values of the detection errors c exceed the predetermined threshold value.

In this way, before calculating the measurement target magnetic field, the measurement apparatus 10 excludes the measurement values i for which the absolute values of the detection errors c are large, and updates the measurement data $\Phi_{Select}$ used by the magnetic field calculating section 930 to calculate the input magnetic field. The measurement values i for which the absolute values of the detection errors c are large correspond to sensors in which a large amount of noise has occurred. According to the measurement apparatus 10 of the present embodiment, since such defective sensors experiencing a large amount of noise are excluded before the detection of the measurement target magnetic field, it is possible to increase the detection accuracy of the measurement target magnetic field.

Figure 11:
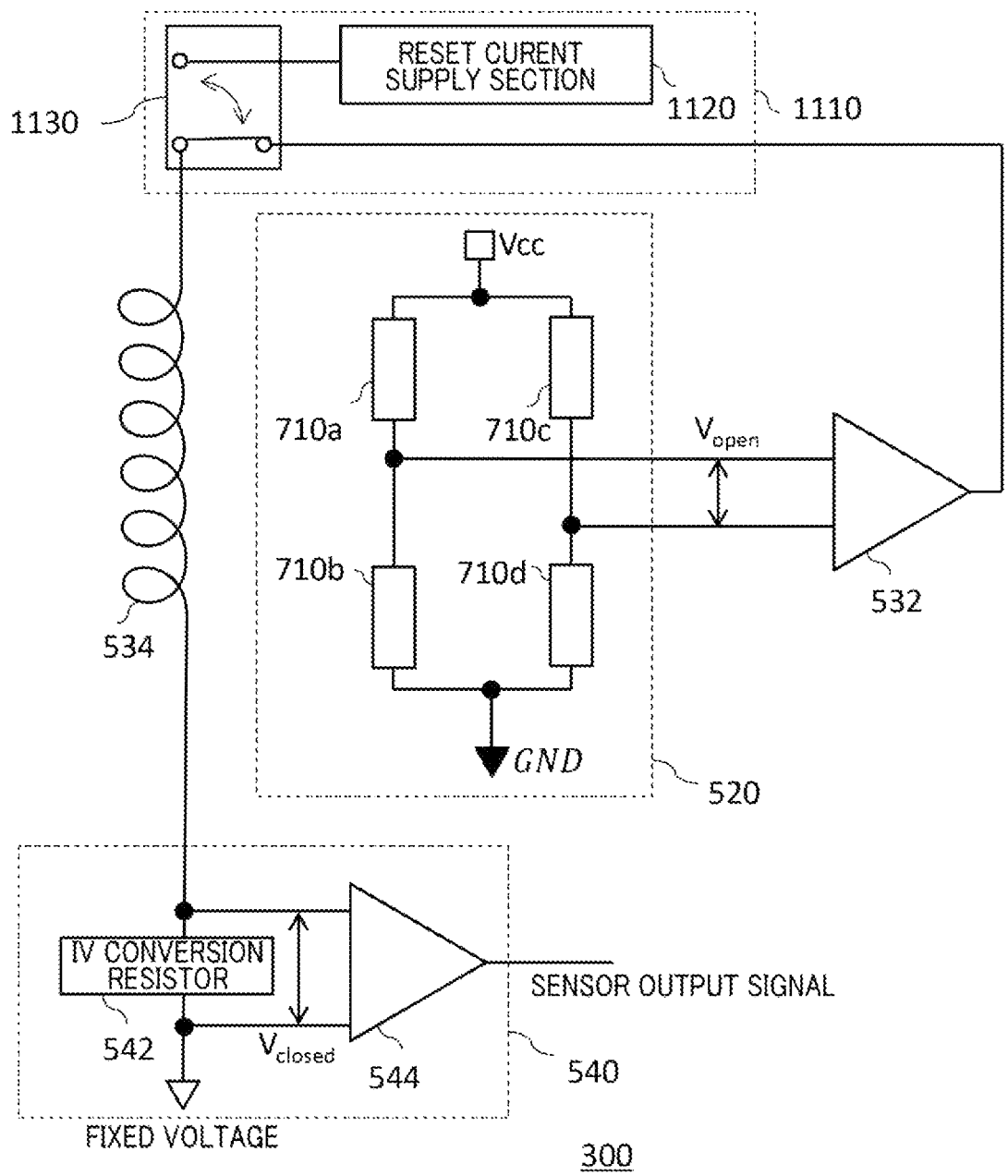
FIG. 11 shows a configuration of a sensor section 300 according to a modification of the present embodiment.

FIG. 11 shows a configuration of a sensor section 300 according to a modification of the present embodiment. In the present drawing, components having the same function and configuration as in FIG. 5 are given the same reference numerals, and the following describes only differing points.

In the present modification, the magnetic sensor 520 includes at least one magnetoresistance effect element. In the present drawing, as an example, the magnetic sensor 520 includes a first magnetoresistance effect element 710*a* and second magnetoresistance effect element 710*b*, which are connected in series between the power supply voltage Vcc and the ground GND, and a third magnetoresistance effect element 710*c* and fourth magnetoresistance effect element 710*d*, which are connected in series between the power supply voltage Vcc and the ground GND. In the present drawing, although omitted from the drawing, the first to fourth magnetoresistance effect elements 710*a* to 710*d* (referred to collectively as "magnetoresistance effect elements 710") may each include a magnetic flux concentrator 720 and a magnetic flux concentrator 730 arranged at respective ends of a magnetoresistance effect element 710, as shown in FIG. 7. The magnetoresistance effect element 710 and magnetic flux concentrators may be positioned to be wrapped within a coil 534. The magnetic sensor 520 outputs each of a voltage between the first magnetoresistance effect element 710*a* and the second magnetoresistance effect element 710*b* and a voltage between the third magnetoresistance effect element 710*c* and the fourth magnetoresistance effect element 710*d*. In the present drawing, a bridge circuit is formed by the first magnetoresistance effect element 710*a*, the second magnetoresistance effect element 710*b*, the third magnetoresistance effect element 710*c*, and the fourth magnetoresistance effect element 710*d*. However, in the magnetic sensor 520, at least one of the first magnetoresistance effect element 710*a*, the second magnetoresistance effect element 710*b*, the third magnetoresistance effect element 710*c*, and the fourth magnetoresistance effect element 710*d* may be formed by a fixed resistance or one of the first magnetoresistance effect element 710*a*, the second magnetoresistance effect element 710*b*, the third magnetoresistance effect element 710*c*, and the fourth magnetoresistance effect element 710*d* may be formed by a fixed voltage source, and the magnetic sensor 520 configuration includes various aspects that output a voltage corresponding to the magnetic field input to at least one magnetoresistance effect element.

When the magnetic sensor 520 includes at least the first magnetoresistance effect element 710a and the second magnetoresistance effect element 710b with opposite polarities from each other connected in parallel and is configured to output the voltage between the first magnetoresistance effect element 710a and the second magnetoresistance effect element 710b, an effect of reducing the fluctuation of characteristics such as offset and sensitivity due to temperature is realized. Here, "opposite polarities" means that, for input magnetic fields in the same direction, the resistance of one magnetoresistance effect element increases and the resistance of the other magnetoresistance effect element decreases. Furthermore, in the present drawing, an example is shown in which the third magnetoresistance effect element 710c and the first magnetoresistance effect element 710a have opposite polarities, the fourth magnetoresistance effect element 710d and the second magnetoresistance effect element 710b have opposite polarities, and, in addition to the first magnetoresistance effect element 710a and the second magnetoresistance effect element 710b having opposite polarities from each other, the third magnetoresistance effect element 710c and the fourth magnetoresistance effect element 710d also have opposite polarities from each other.

In the present modification, the output terminals of the magnetic sensor 520 are connected respectively to two differential input terminals of the amplification circuit 532. The amplification circuit 532 generates a feedback current corresponding to the difference between the respective output voltages of the magnetic sensor 520, and supplies this feedback current to the coil 534. Here, the difference between the respective output voltages of the magnetic sensor 520 is defined as Vopen.

In the present modification, the output section 540 includes a current-voltage conversion resistor 542 and an operational amplifier 544.

The current-voltage conversion resistor 542 has one end connected to the coil 534 and the other end connected to a fixed voltage, converts the feedback current into a voltage, and generates a current (feedback current×resistance value of the current-voltage conversion resistor 542) that is based on the feedback current at the respective ends thereof. Here, the voltage based on the feedback current generated by the current-voltage conversion resistor 542 is defined as Vclosed.

The ends of the current-voltage conversion resistor 542 are connected respectively to the differential input terminals of the operational amplifier 544, and the operational amplifier 544 outputs the voltage across the ends of the current-voltage conversion resistor 542, i.e. the voltage corresponding to the voltage Vclosed.

In the present modification, the sensor section 300 further includes a magnetic resetting section 1110. The magnetic resetting section 1110 applies to the magnetic sensor 520 a reset magnetic field to magnetically saturate the magnetic sensor 520, in the reset phase. The magnetic resetting section 1110 includes a reset current supplying section 1120 and a switching section 1130.

In the reset phase, the reset current supplying section 1120 supplies a reset current to the coil 534, causing the coil 534 to generate the reset magnetic field that magnetically saturates each magnetoresistance effect element of the magnetic sensor 520. Magnetic saturation means that a constant magnetic field is input to the magnetoresistance effect element and the output magnetoresistance effect element does not fluctuate with respect to the magnetic field. In this way, a magnetic field that magnetically saturates a magnetoresistance effect element is defined as a reset magnetic field, and a current that causes the generation of the reset magnetic field is defined as the reset current.

The switching section 1130 switches whether the feedback current for generating the feedback magnetic field is supplied to the magnetic field generating section 530. In a state where the feedback current is not being supplied to the magnetic field generating section 530, the reset current supplying section 1120 supplies the magnetic field generating section 530 with the reset current to cause the magnetic field generating section 530 to generate the reset magnetic field. For example, the switching section 1130 is provided between the amplification circuit 532 and the coil 534, and connects the coil 534 to the reset current supplying section 1120 when the feedback current generated by the amplification circuit 532 is not to be supplied to the coil 534. In a state where the feedback current is not being supplied to the coil 534, the reset current supplying section 1120 may supply the reset current to the coil 534 to cause the coil 534 to generate the reset magnetic field.

In this way, in the present modification, in the sensor section 300, when the input magnetic field for the sensor section 300 is input to the magnetic sensor 520, the amplification circuit 532 generates a feedback current corresponding to a difference (i.e. the voltage Vopen) between the respective voltages of the magnetic sensor 520 corresponding to the input magnetic field, and supplies this voltage difference to the coil 534. The coil 534 generates the feedback magnetic field that cancels output the input magnetic field input to the magnetic sensor 520, according to the feedback current supplied thereto. Then, in the measurement phase, the output section 540 outputs a measurement value corresponding to the feedback current generated for the input magnetic field, specifically a voltage value corresponding to the voltage Vclosed. Here, this series of controls are defined as the closed loop control. During the closed loop control, control is performed such that the value of the voltage Vopen becomes zero, that is, such that a feedback magnetic field cancelling out the input magnetic field is generated.

The above describes an example of a case in which the coil 534 is used as both the coil for generating the feedback magnetic field and the coil for generating the reset magnetic field, but the present modification is not limited to this. The sensor section 300 may include, as the coil for generating the reset magnetic field, a coil that is separate from the coil 534 for generating the feedback magnetic field. Furthermore, the above describes an example of a case in which the sensor section 300 includes all of the magnetic resetting section 1110, but the present modification is not limited to this. A portion of the magnetic resetting section 1110, e.g. the reset current supplying section 1120, does not need to be provided in the sensor section 300, and may be provided in the sensor data gathering section 230 instead, for example.

Figure 12:
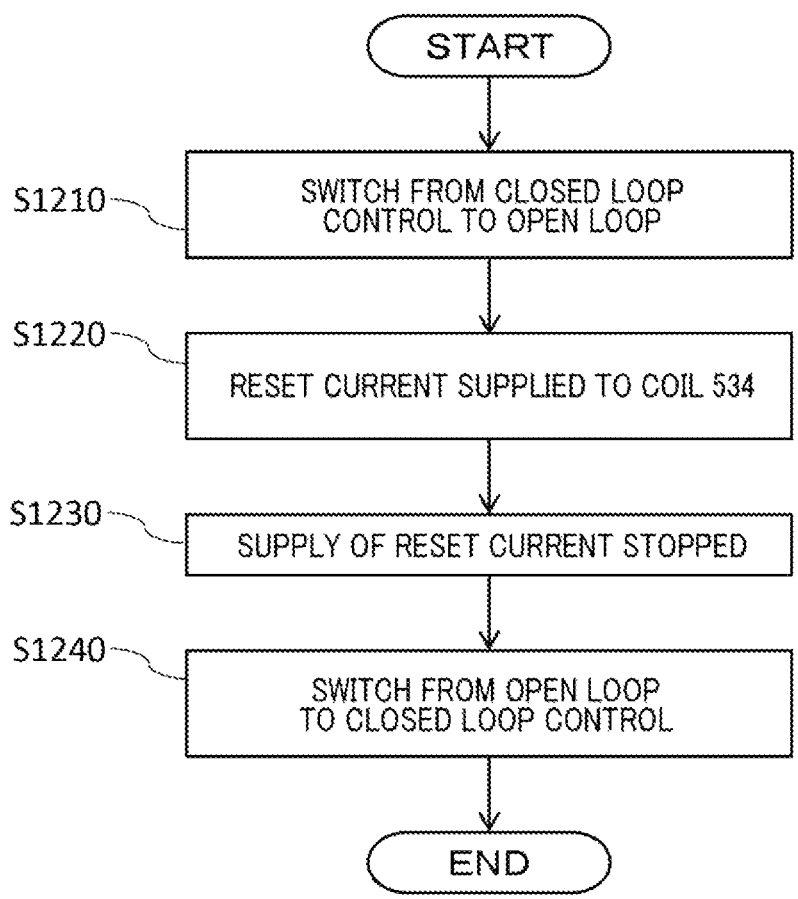
FIG. 12 shows an example of a procedure of a magnetic reset in the reset phase performed by the sensor section 300 according to the present modification.

FIG. 12 shows an example of a procedure of a magnetic reset in the reset phase performed by the sensor section 300 according to the present modification. Here, a state in which the closed loop control is not performed is defined as an open loop. At step 1210, the switching section 1130 switches from the closed loop control to a state in which the feedback current is not supplied to the coil 534, i.e. to the open loop. Furthermore, the switching section 1130 connects the coil 534 to the reset current supplying section 1120.

Next, at step 1220, the reset current supplying section 1120 supplies the reset current to the coil 534, causing the coil 534 to generate the reset magnetic field. Here, the reset current supplying section 1120 may supply a current with a magnitude predetermined to be enough to magnetically saturate each magnetoresistance effect element of the magnetic sensor 520, to cause the coil 534 to generate the reset magnetic field. Instead, the reset current supplying section 1120 may gradually increase the strength of the supplied reset current while monitoring the output voltage of the magnetic sensor 520, until the output voltage of the magnetic sensor 520 becomes a value indicating that each magnetoresistance effect element has been magnetically saturated, to cause the coil 534 to generate the reset magnetic field. The reset magnetic field may be set to be greater than or equal to a magnitude obtained by adding a geomagnetic component to the magnitude of the magnetic field that magnetically saturates the magnetoresistance effect element in a state where the magnetic field is 0, for example, such that it is possible to magnetically saturate the magnetoresistance effect element no matter what direction the sensor section 300 is arranged in, that is, no matter what direction the geomagnetism is oriented in.

Next, at step 1230, the reset current supplying section 1120 stops the supply of the reset current to the coil 534. Here, after the coil 534 has generated the reset magnetic field and each magnetoresistance effect element has been magnetically saturated, the reset current supplying section 1120 gradually reduces the magnitude of the reset current supplied to the coil 534, to gradually reduce the strength of the reset magnetic field generated by the coil 534. Usually, when a magnetic field is gradually added to a magnetoresistance effect element, a domain wall (a boundary between magnetic domains) moves, and then rotation of magnetization occurs in the magnetic domains, and eventually a single domain state is formed, which is entirely covered by one magnetic domain. This corresponds to magnetic saturation. Then, in the magnetoresistance effect element, when the magnetic field is reduced from the state of magnetic saturation, a domain wall having various magnetic directions occurs to minimize the energy of the magnetoresistance effect element, and the domain wall moves along with the decrease of the magnetic field. According to the reset current supplying section 1120 of the sensor section 300 according to the present modification, at step 1230 after the magnetic saturation of each magnetoresistance effect element, the reset magnetic field supplied to the coil 534 is gradually reduced, thereby making it possible for the magnetoresistance effect element to always approach the same magnetization state. Due to this, the magnetoresistance effect element becomes the same state after every magnetic reset, and therefore variations in the magnetic state of the magnetoresistance effect element after each magnetic reset can be made relatively small.

At step 1240, the switching section 1130 connects the coil 534 to the amplification circuit 532, switches from the open loop to the closed loop control, and ends the magnetic reset process. After this, in the measurement phase, according to the closed loop control, the output section 540 outputs the measurement value corresponding to the feedback current generated for the input magnetic field.

Figure 13:
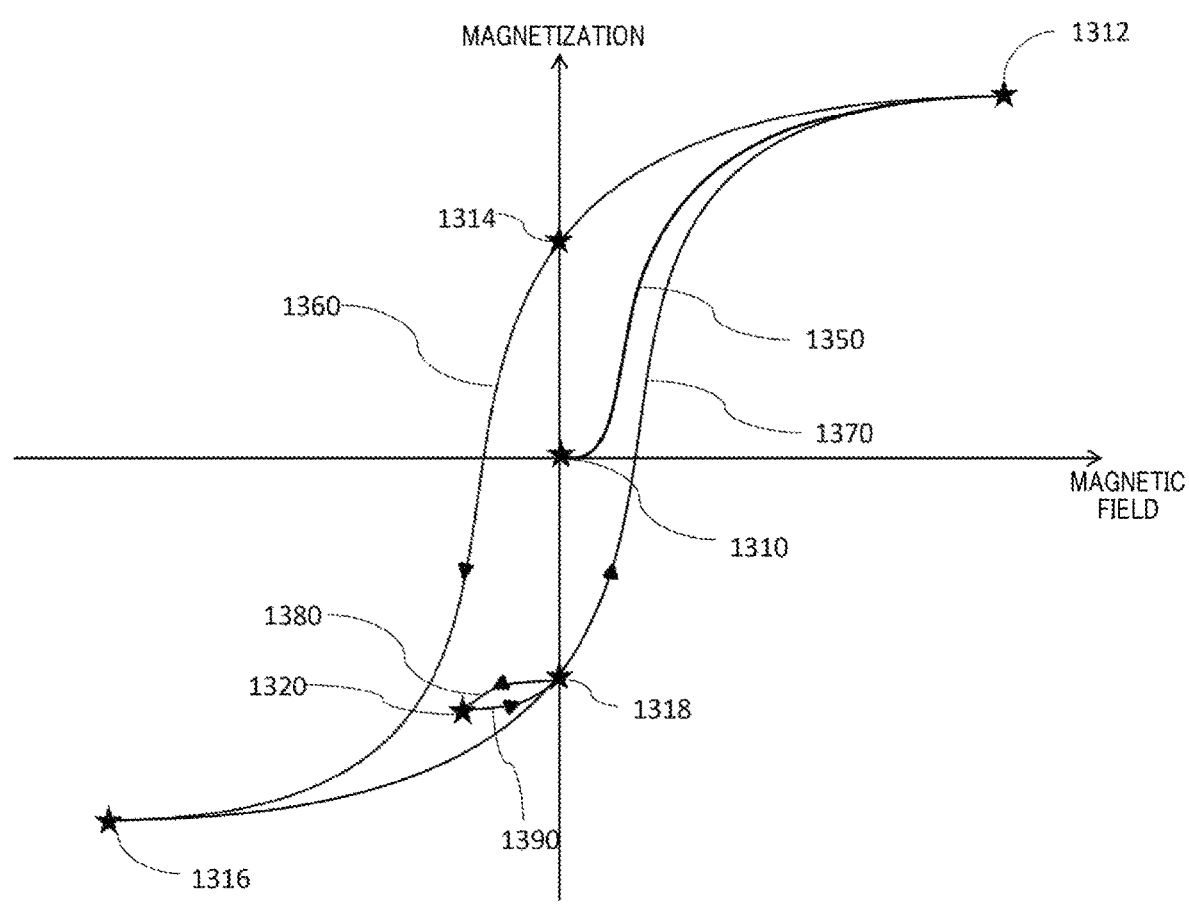
FIG. 13 shows magnetization curves of a general magnetic body.

FIG. 13 shows magnetization curves of a general magnetic body. As shown by point 1310, in the initial magnetization state, the magnetic body has a magnetization of 0 when the magnetic field is 0. When a magnetic field is gradually increased to the positive side from this state, the magnetization increases along the curve 1350 and reaches the point 1312. This curve 1350 is referred to as an initial magnetization curve. Upon reaching the point 1312, the magnetization does not change even when the magnetic field is further increased to the positive side. At this time, the magnetic body is in the magnetically saturated state. After this, the magnetic field is gradually reduced, and the magnetization travels along the curve 1360, instead of the curve 1350, and reaches the point 1314. At the point 1314, magnetization remains even through the magnetic field is 0, and this is referred to as residual magnetization. Furthermore, when the magnetic field is gradually increased to the negative side, the magnetization decreases along the curve 1360 and reaches the point 1316. Upon reaching the point 1316, the magnetization does not change even when the magnetic field is further increased to the negative side. At this time, the magnetic body is again in the magnetically saturated state. After this, when the magnetic field is again gradually increased to the positive side, the magnetization increases along the curve 1370, instead of the curve 1360, and passes through the point 1318 to reach the point 1312. Generally, a magnetic body has such a magnetic hysteresis characteristic. Here, the largest loop formed from the curve 1360 and the curve 1370 passing through the point 1312 and the point 1316 where the magnetic body is in the magnetically saturated state is referred to as a major loop.

On the other hand, when the magnetic field is gradually increased to the positive side from the state of the point 1318, for example, the magnetization decreases along the curve 1380. From this state, when the magnetic field is again gradually increased to the positive side at the point 1320 before the magnetic body is magnetically saturated, the magnetization increases along the curve 1390, instead of the curve 1380, and reaches the point 1318. In this way, the loop formed by the curve 1380 and the curve 1390, for example, that does not pass through the points 1312 and 1316 where the magnetic body is in the magnetically saturated state is referred to as a minor loop.

Figure 14:
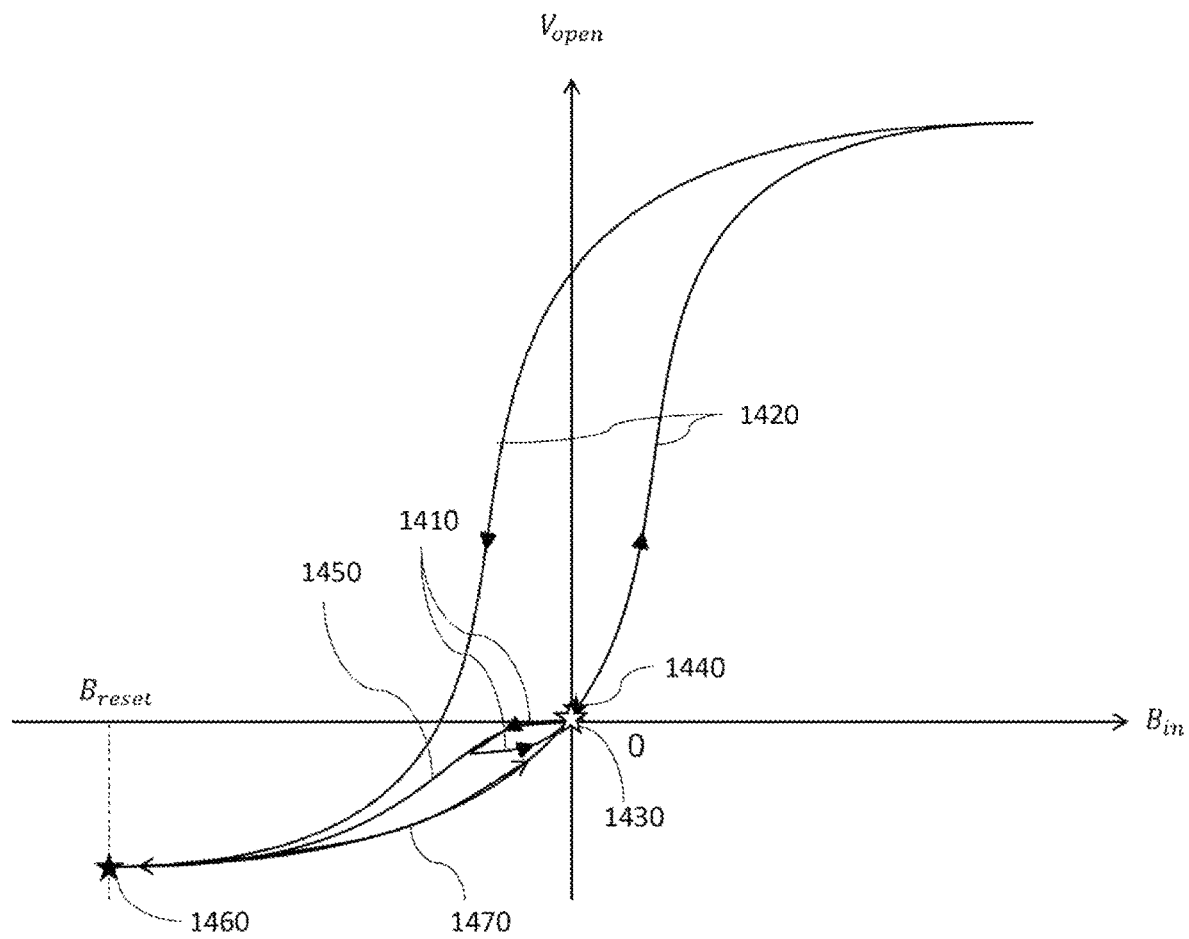
FIG. 14 shows a characteristic of the voltage Vopen with respect to the input magnetic field Bin input to the magnetic sensor 520, in the sensor section 300 according to the present modification.

FIG. 14 shows a characteristic of the voltage Vopen with respect to the input magnetic field Bin input to the magnetic sensor 520, in the sensor section 300 according to the present modification. In the present modification, the characteristic of the voltage Vopen with respect to the input magnetic field Bin input to the magnetic sensor 520 is a characteristic such as shown in the present drawing, according to the magnetic hysteresis characteristic of the first magnetoresistance effect element 710*a*, the second magnetoresistance effect element 710*b*, the third magnetoresistance effect element 710*c*, and the fourth magnetoresistance effect element 710*d* of the magnetic sensor 520. The reference numeral 1410 indicates the minor loop, and the reference numeral 1420 indicates the major loop.

With the sensor section 300 according to the present modification, when the measurement of the magnetic field is performed according to the closed loop control in a state prior to the magnetic reset being performed, the magnetic field is measured in the state where the magnetic operation point of each magnetoresistance effect element of the magnetic sensor 520 is at the point 1430 on the minor loop 1410. However, as a general phenomenon in a magnetic body, in a case where each magnetoresistance effect element of the magnetic sensor 520 operates on the minor loop, it is impossible to realize a magnetic sensitivity (rate of change of the voltage Vopen with respect to Bin) as high as in a case where each magnetoresistance effect element operates on the major loop, and it is impossible to detect a very weak measurement target magnetic field. Therefore, with the measurement apparatus 10 in which the plurality of magnetic sensor cells 220 each include the sensor sections 300 according to the present modification, before detecting the measurement target magnetic field, the magnetic sensors 520 detected as being defective sensors with a large amount of noise are magnetically reset.

Figure 15:
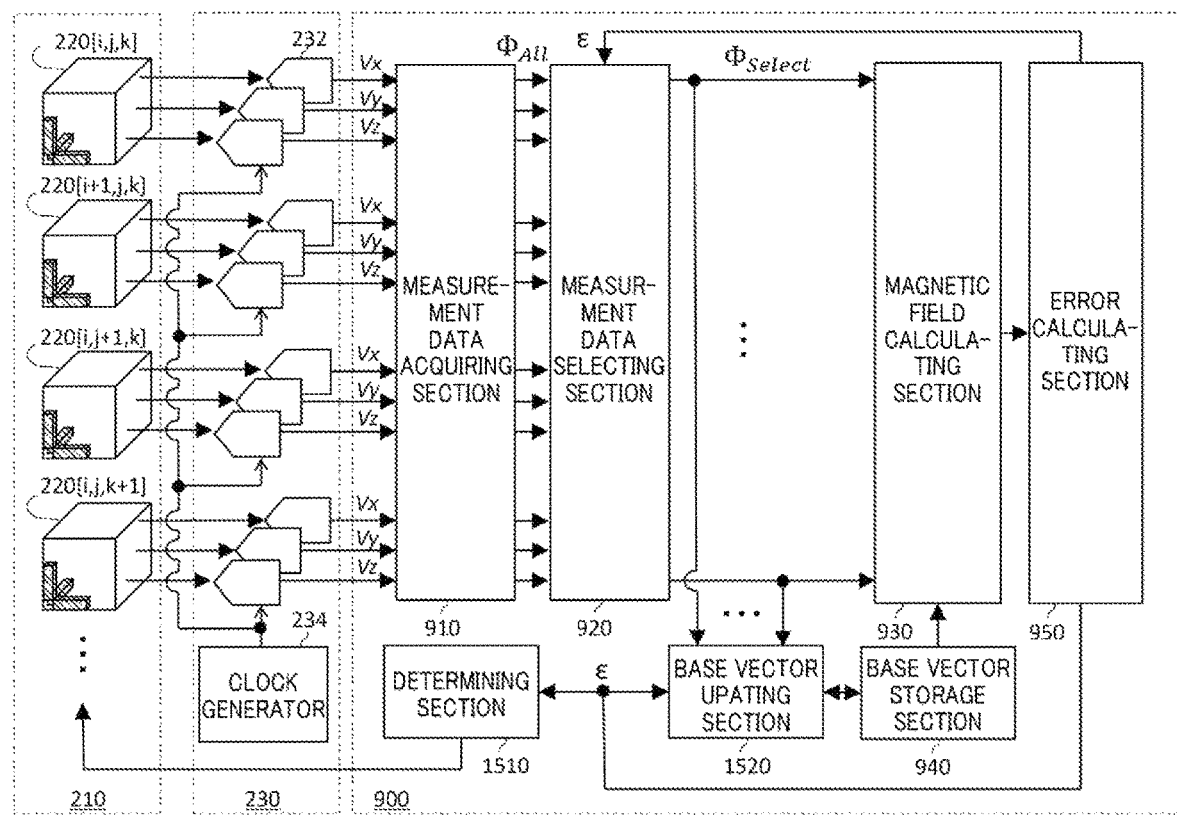
FIG. 15 shows a configuration of a magnetic sensor array 210, a sensor data gathering section 230, and a sensor data processing section 900 in a case where each of the plurality of magnetic sensor cells 220 includes the sensor sections 300 according to the present modification.

FIG. 15 shows a configuration of a magnetic sensor array 210, a sensor data gathering section 230, and a sensor data processing section 900 in a case where each of the plurality of magnetic sensor cells 220 includes the sensor sections 300 according to the present modification. In the present drawing, components having the same function and configuration as in FIG. 9 are given the same reference numerals, and the following describes only differing points. In the present modification, the plurality of magnetic sensor cells 220 included in the magnetic sensor array 210 include the sensor sections 300 shown in FIG. 11, for example. In other words, each sensor section 300 included in the plurality of magnetic sensor cells 220 is configured to be capable of magnetically resetting the magnetic sensor 520 in the reset phase. Furthermore, in the present modification, the sensor data processing section 900 further includes a determining section 1510 and a base vector updating section 1520.

The determining section 1510 determines whether to reset at least one of the plurality of magnetic sensor cells 220, based on the detection errors ε supplied from the error calculating section 950. More specifically, the determining section 1510 makes a determination to reset a magnetic sensor cell 220 that includes a magnetic sensor 520 used to acquire a measurement value for which the magnetic field detection error ε is outside a predetermined range. In this case, the determining section 1510 may make a determination to reset only the magnetic sensor 520 used to acquire the measurement value for which the detection error ε is outside the predetermined range, or may make a determination to reset all of the magnetic sensors 520 of the magnetic sensor cell 220 including this magnetic sensor 520.

The base vector updating section 1520 updates the base vectors, based on the detection errors ε. After the magnetic sensor 520 used to acquire the measurement value for which the detection error ε is outside the predetermined range has been magnetically reset, the magnetic field calculating section 930 recalculates the input magnetic field. At this time, the magnetic field calculating section 930 uses the base vector that has been updated by the base vector updating section 1520. The following describes this in detail.

Figure 16:
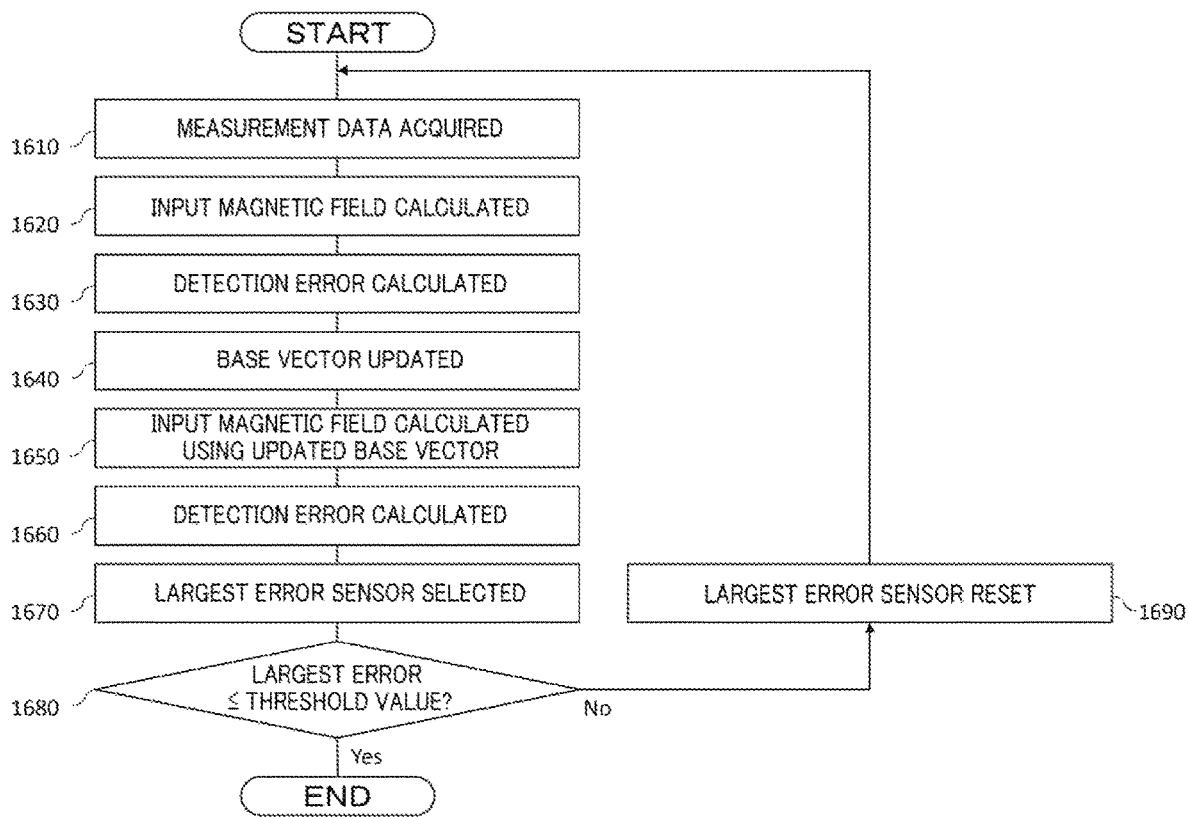
FIG. 16 shows an example of a procedure for resetting a defective sensor, as pre-processing for calculating the measurement target magnetic field by the measurement apparatus 10 in which each of the plurality of magnetic sensor cells 220 includes the sensor sections 300 according to the present modification.

FIG. 16 shows an example of a procedure for resetting a defective sensor, as pre-processing for calculating the measurement target magnetic field by the measurement apparatus 10 in which each of the plurality of magnetic sensor cells 220 includes the sensor sections 300 according to the present modification. At step 1610, the measurement apparatus 10 acquires the measurement data. For example, the measurement data acquiring section 910 acquires a plurality of measurement values (the measurement data $\Phi_{All}$) that are based on the input magnetic field measured by the sensor sections 300x to 300z in the plurality of magnetic sensor cells 220 forming the magnetic sensor array 210.

At step 1620, the measurement apparatus 10 calculates the input magnetic field. In this procedure, the measurement data selecting section 920 selects all of the plurality of measurement values as the measurement data $\Phi_{Select}$ ($\Phi_{All}=\Phi_{Select}$). The magnetic field calculating section 930 calculates the input magnetic field using the same method as in step 1020, based on the measurement data $\Phi_{All}$.

At step 1630, the measurement apparatus 10 calculates the detection error ε. For example, the error calculating section 950 calculates the detection error ε using the same technique as in step 1030.

At step 1640, the measurement apparatus 10 updates the base vector. For example, the base vector updating section 1520 updates the base vector using the least square technique, in a manner to minimize the detection error ε calculated at step 1630. As a specific example, the base vector is updated by performing an algorithm that minimizes ε defined by Expression 13 based on optimization theory and updating the calibration coefficient matrix K in Expression 7. This calibration coefficient matrix K includes vectors expressing the magnetosensitive axis direction and the magnetic sensitivity of the sensor sections 300x, 300y, and 300z of the plurality of magnetic sensor cells 220. Accordingly, the base vector updating section 1520 can correct the magnetic sensitivity (main axis sensitivity and other axis sensitivity) of each magnetic sensor cell 220 by updating this calibration coefficient matrix K.

At step 1650, the measurement apparatus 10 calculates the input magnetic field using the updated base vector that was updates at step 1640. For example, the magnetic field calculating section 930 calculates the input magnetic field with the same technique as in step 1020, using the updated base vector.

At step 1660, the measurement apparatus 10 calculates the detection error ε. For example, the error calculating section 950 calculates the detection error ε using the same technique as in step 1030.

At step 1670, the measurement apparatus 10 selects a maximum error sensor which has the largest absolute value for the detection error ε(maximum error). For example, the determining section 1510 specifies the measurement value having the largest absolute value for the detection error ε, based on the detection error ε of each measurement value supplied from the error calculating section 950, and selects the magnetic sensor 520 used to acquire this measurement value as the maximum error sensor.

At step 1680, the measurement apparatus 10 judges whether the maximum error is less than or equal to a predetermined threshold value. For example, the determining section 1510 may judge whether the absolute value of the detection error ε of the maximum error sensor selected at step 1670 is less than or equal to a predetermined threshold value Max_E_Th.

At step 1680, if it is judged that the maximum error is less than or equal to the predetermined threshold value, the measurement apparatus 10 ends the process of the procedure for resetting the defective sensors.

On the other hand, at step 1680, if it is judged that the maximum error exceeds the predetermined threshold value, at step 1690, the determining section 1510 makes a determination to reset the magnetic sensor 520 selected as the maximum error sensor at step 1670. In this case, the determining section 1510 may make a determination to reset only the magnetic sensor 520 used to acquire the measurement value for which the detection error ε is outside the predetermined range, or may make a determination to reset all of the magnetic sensors 520 of the magnetic sensor cell 220 that includes this magnetic sensor 520. The determining section 1510 issues instructions for a reset to the magnetic sensor cell 220 including the magnetic sensor 520 determined to be reset. The magnetic sensor cell 220 instructed to be reset switches the magnetic sensor 520 that is the reset target from the closed loop control to the open loop, in accordance with the procedure of FIG. 12, transitions this magnetic sensor 520 to the reset phase, and magnetically resets this magnetic sensor 520.

At step 1690, after the magnetic sensor 520 used to acquire the measurement value for which the detection error ε is outside the predetermined range has been magnetically reset, the process returns to step 1610, and the magnetic field calculating section 930 recalculates the input magnetic field using the newly acquired measurement data. At step 1680, the measurement apparatus 10 repeats this process until it is judged that the maximum error is less than or equal to the predetermined threshold value. At this time, the measurement apparatus 10 repeats this process without cutting the feedback current (i.e. under the closed loop control) for the magnetic sensors that are not being magnetically reset.

In this way, the determining section 1510 determines whether to reset at least one of the plurality of magnetic sensor cells 220, based on the detection error ε of the magnetic field supplied from the error calculating section 950. More specifically, the determining section 1510 makes a determination to reset the magnetic sensor cell 220 including the magnetic sensor 520 used to acquire a measurement value for which the magnetic field detection error ε is outside the predetermined range.

The above describes an example of a case in which the measurement apparatus 10 first selects one maximum error sensor for which the detection error ε is relatively the largest and, when it is judged that the maximum error exceeds the predetermined threshold value, magnetically resets this maximum error sensor. However, the present embodiment is not limited to this. The measurement apparatus 10 may magnetically reset one or more magnetic sensors 520 for which the absolute values of the detection errors c exceed the predetermined threshold value.

Furthermore, when the absolute value of the detection error ε does not drop below the predetermined threshold value even after at least a predetermined number of magnetic resets have been performed, a determination may be made to not use the magnetic sensor 520 that was used to acquire this measurements value in the detection of the measurement target magnetic field, and the process may be ended.

In this way, the measurement apparatus 10 magnetically resets the magnetic sensors 520 used to acquire the measurement values for which the absolute values of the detection errors ε are large, and redetects the input magnetic field. A magnetic sensor 520 used to acquire a measurement value for which the absolute value of the detection error ε is large could be a defective sensor that has reduced magnetic sensitivity caused by a magnetic history or an increased amount of noise. According to the measurement apparatus 10 of the present modification, the magnetic sensitivity is increased by magnetically resetting defective sensors that have reduced magnetic sensitivities or an increased amount of noise, before detecting the measurement target magnetic field, and therefore it is possible to increase the calculation accuracy of the measurement target magnetic field.

The embodiment described above and other embodiments may each function independently, or may be combined to function together. That is, for example, after the procedure for resetting defective sensors according to FIG. 16 has been performed as pre-processing before the detection of the measurement target magnetic field, the procedure for excluding defective sensors according to FIG. 10 may be performed. By combining these embodiments, it is possible to further increase the detection accuracy of the measurement target magnetic field.

Furthermore, the embodiments above show examples of a case in which the measurement apparatus 10 calculates the input magnetic field after the measurement values i for which the absolute values of the detection errors c are large are excluded. However, the present invention is not limited to this.

For example, by solving the spatial distribution of the magnetic field using Expression 11, the magnetic field calculating section 930 can, based on a plurality of measurement values selected by the measurement data selecting section 920, recalculate the input magnetic field at a location where the plurality of measurement values were measured. In this case, the error calculating section 950 may calculate the detection error based on the detection result of the input magnetic field at the location where the plurality of recalculated measurement values were measured.

As an example, by solving the spatial distribution of the magnetic field using Expression 11, the magnetic field calculating section 930 can express the magnetic field vector B(r) at the coordinates (position vector=r, coordinates shown as polar coordinates=(r, θ, φ) of a sensor that measured a measurement value i excluded from the signal space separation calculation, using the coefficients relating to the calculation result of the input magnetic field, i.e. ^Xin and ^Xout of FIG. 11.

$$B(r) = -\mu \sum_{l=1}^{Lin} \sum_{m=-l}^{l} \hat{X}_{in}(l, m) \cdot \nabla \left( \frac{1}{r^{l+1}} \cdot Y_{l,m}(\theta, \varphi) \right) - \mu \sum_{l=1}^{Lout} \sum_{m=-l}^{l} \hat{X}_{out}(l, m) \cdot \nabla \left( r^{l} \cdot Y_{l,m}(\theta, \varphi) \right)$$

Expression 15

In other words, based on the coefficients relating to the calculation of the input magnetic field calculated from the plurality of measurement values selected by the measurement data selecting section 920, the magnetic field calculating section 930 can calculate the input magnetic field at a location where an excluded measurement value i was measured. Therefore, since the measurement apparatus 10 reconstructs the magnetic field of defective sensors using Expression 15, it is possible to restrict a decrease in the magnetic field measurement accuracy caused by dropping the measurement values at the positions of defective sensors. Accordingly, the measurement apparatus 10 can perform the magnetic field detection with high accuracy.

Various embodiments of the present invention may be described with reference to flowcharts and block diagrams whose blocks may represent (1) steps of processes in which operations are performed or (2) sections of apparatuses responsible for performing operations. Certain steps and sections may be implemented by dedicated circuitry, programmable circuitry supplied with computer-readable instructions stored on computer-readable media, and/or processors supplied with computer-readable instructions stored on computer-readable media. Dedicated circuitry may include digital and/or analog hardware circuits and may include integrated circuits (IC) and/or discrete circuits. Programmable circuitry may include reconfigurable hardware circuits comprising logical AND, OR, XOR, NAND, NOR, and other logical operations, flip-flops, registers, memory elements, etc., such as field-programmable gate arrays (FPGA), programmable logic arrays (PLA), and the like.

The computer-readable medium may be a tangible device that can store instructions to be executed by a suitable device, and as a result, a computer-readable medium having instructions stored thereon is a product that includes instructions that can be executed in order to create the means for executing the operations designated by flow charts and block diagrams. Examples of the computer-readable medium may include an electronic storage device, a magnetic storage device, an optical storage device, an electromagnetic recording medium, a magnetic recording medium, an optical recording medium, an electromagnetic recording medium, a semiconductor recording medium, and the like. Specific examples of the computer-readable medium may include a floppy (registered trademark) disk, a diskette, a hard disk, a random access memory (RAM), a read-only memory (ROM), an erasable programmable read-only memory (EPROM or Flash memory), an electrically erasable programmable read-only memory (EEPROM), a static random access memory (SRAM), a portable compact disc read-only memory (CD-ROM), a digital versatile disk (DVD), a Blu-ray (registered trademark) disk, a memory stick, an integrated circuit card, or the like.

The computer-readable instructions may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, JAVA (registered trademark), C++ or the like, and conventional procedural programming languages, such as the "C" programming language or similar programming languages.

The computer-readable instructions may be provided to a processor or programmable circuitry of a general purpose computer, special purpose computer, or other programmable data processing apparatus to produce a machine, either locally, via a local area network (LAN), or via a wide area network (WAN) such as the Internet, and may be executed to create the means for performing the operations designated by the flow charts and block diagrams. Examples of the processor include a computer processor, a processing unit, a microprocessor, a digital signal processor, a controller, a microcontroller, and the like.

Figure 17:
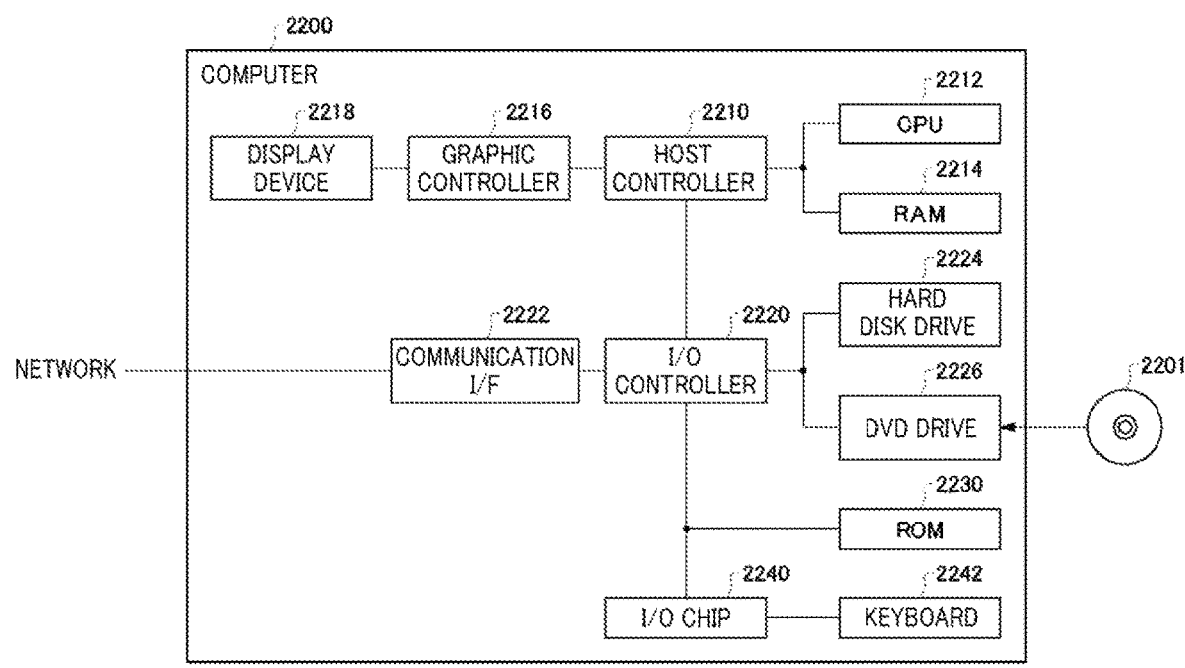
FIG. 17 shows an example of a computer 2200 in which aspects of the present invention may be wholly or partly embodied.

FIG. 17 shows an example of a computer 2200 in which aspects of the present invention may be wholly or partly embodied. A program that is installed in the computer 2200 can cause the computer 2200 to function as or perform operations associated with apparatuses of the embodiments of the present invention or one or more sections thereof, and/or cause the computer 2200 to perform processes of the embodiments of the present invention or steps thereof. Such a program may be executed by the CPU 2212 to cause the computer 2200 to perform certain operations associated with some or all of the blocks of flowcharts and block diagrams described herein.

The computer 2200 according to the present embodiment includes a CPU 2212, a RAM 2214, a graphic controller 2216, and a display device 2218, which are mutually connected by a host controller 2210. The computer 2200 also includes input/output units such as a communication interface 2222, a hard disk drive 2224, a DVD-ROM drive 2226 and an IC card drive, which are connected to the host controller 2210 via an input/output controller 2220. The computer also includes legacy input/output units such as a ROM 2230 and a keyboard 2242, which are connected to the input/output controller 2220 through an input/output chip 2240.

The CPU 2212 operates according to programs stored in the ROM 2230 and the RAM 2214, thereby controlling each unit. The graphic controller 2216 obtains image data generated by the CPU 2212 on a frame buffer or the like provided in the RAM 2214 or in itself, and causes the image data to be displayed on the display device 2218.

The communication interface 2222 communicates with other electronic devices via a network. The hard disk drive 2224 stores programs and data used by the CPU 2212 within the computer 2200. The DVD-ROM drive 2226 reads the programs or the data from the DVD-ROM 2201, and provides the hard disk drive 2224 with the programs or the data via the RAM 2214. The IC card drive reads programs and data from an IC card, and/or writes programs and data into the IC card.

The ROM 2230 stores therein a boot program or the like executed by the computer 2200 at the time of activation, and/or a program depending on the hardware of the computer 2200. The input/output chip 2240 may also connect various input/output units via a parallel port, a serial port, a keyboard port, a mouse port, and the like to the input/output controller 2220.

A program is provided by computer readable media such as the DVD-ROM 2201 or the IC card. The program is read from the computer readable media, installed into the hard disk drive 2224, RAM 2214, or ROM 2230, which are also examples of computer readable media, and executed by the CPU 2212. The information processing described in these programs is read into the computer 2200, resulting in cooperation between a program and the above-mentioned various types of hardware resources. An apparatus or method may be constituted by realizing the operation or processing of information in accordance with the usage of the computer 2200.

For example, when communication is performed between the computer 2200 and an external device, the CPU 2212 may execute a communication program loaded onto the RAM 2214 to instruct communication processing to the communication interface 2222, based on the processing described in the communication program. The communication interface 2222, under control of the CPU 2212, reads transmission data stored on a transmission buffering region provided in a recording medium such as the RAM 2214, the hard disk drive 2224, the DVD-ROM 2201, or the IC card, and transmits the read transmission data to a network or writes reception data received from a network to a reception buffering region or the like provided on the recording medium.

In addition, the CPU 2212 may cause all or a necessary portion of a file or a database to be read into the RAM 2214, the file or the database having been stored in an external recording medium such as the hard disk drive 2224, the DVD-ROM drive 2226 (DVD-ROM 2201), the IC card, etc., and perform various types of processing on the data on the RAM 2214. The CPU 2212 may then write back the processed data to the external recording medium.

Various types of information, such as various types of programs, data, tables, and databases, may be stored in the recording medium to undergo information processing. The CPU 2212 may perform various types of processing on the data read from the RAM 2214, which includes various types of operations, processing of information, condition judging, conditional branch, unconditional branch, search/replace of information, etc., as described throughout this disclosure and designated by an instruction sequence of programs, and writes the result back to the RAM 2214. In addition, the CPU 2212 may search for information in a file, a database, etc., in the recording medium. For example, when a plurality of entries, each having an attribute value of a first attribute associated with an attribute value of a second attribute, are stored in the recording medium, the CPU 2212 may search for an entry matching the condition whose attribute value of the first attribute is designated, from among the plurality of entries, and read the attribute value of the second attribute stored in the entry, thereby obtaining the attribute value of the second attribute associated with the first attribute satisfying the predetermined condition.

The above-explained program or software modules may be stored in the computer readable media on or near the computer 2200. In addition, a recording medium such as a hard disk or a RAM provided in a server system connected to a dedicated communication network or the Internet can be used as the computer readable media, thereby providing the program to the computer 2200 via the network.

While the embodiments of the present invention have been described, the technical scope of the invention is not limited to the above described embodiments. It will be apparent to persons skilled in the art that various alterations and improvements can be added to the above-described embodiments. It should also apparent from the scope of the claims that the embodiments added with such alterations or improvements are within the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. A measurement apparatus comprising:
a magnetic sensor array that is formed by three-dimensionally arranging a plurality of magnetic sensor cells that each include a magnetic sensor, and is capable of detecting an input magnetic field in three axial directions;
a measurement data acquiring section that acquires a plurality of measurement values based on the input magnetic field detected by the magnetic sensor array;
a magnetic field calculating section that calculates the input magnetic field based on the plurality of measurement values;
an error calculating section that calculates a detection error of the input magnetic field, based on the plurality of measurement values and a calculation result obtained by calculating the input magnetic field; and
a measurement data selecting section that selects a plurality of measurement values to be used for calculating the input magnetic field by the magnetic field calculating section, from among the plurality of measurement values, based on the detection error, wherein
the magnetic field calculating section performs signal separation on a spatial distribution of the input magnetic field indicated by the plurality of measurement values, with a signal vector having components that are signals output by the respective magnetic sensors when the magnetic sensor array detects a magnetic field having a spatial distribution of an orthonormal function serving as a base vector, and
the error calculating section calculates the detection error based on a result obtained by the signal separation performed by the magnetic field calculating section.

2. A measurement apparatus comprising:
a magnetic sensor array that is formed by three-dimensionally arranging a plurality of magnetic sensor cells that each include a magnetic sensor, and is capable of detecting an input magnetic field in three axial directions;
a measurement data acquiring section that acquires a plurality of measurement values based on the input magnetic field detected by the magnetic sensor array;
a magnetic field calculating section that calculates the input magnetic field based on the plurality of measurement values;
an error calculating section that calculates a detection error of the input magnetic field, based on the plurality of measurement values and a calculation result obtained by calculating the input magnetic field; and
a measurement data selecting section that selects a plurality of measurement values to be used for calculating the input magnetic field by the magnetic field calculating section, from among the plurality of measurement values, based on the detection error, wherein
the error calculating section calculates the detection error for each of the plurality of measurement values,
the measurement data selecting section selects the plurality of measurement values after excluding a measurement value for which the detection error is outside a predetermined range, and
the magnetic field calculating section recalculates the input magnetic field after the measurement value for which the detection error is outside the predetermined range has been excluded.

3. The measurement apparatus according to claim 2, wherein
the magnetic field calculating section recalculates, based on the plurality of measurement values selected by the measurement data selecting section, the input magnetic field at locations where the plurality of measurement values selected by the measurement data selecting section were measured, and
the error calculating section calculates the detection error based on a detection result of the input magnetic field at the locations where the plurality of measurement values selected by the measurement data selecting section were measured.

4. The measurement apparatus according to claim 2, wherein
the magnetic field calculating section calculates the input magnetic field at a location where the excluded measurement value was measured, based on a coefficient relating to a calculation result of the input magnetic field calculated from the plurality of measurement values selected by the measurement data selecting section.

5. The measurement apparatus according to claim 1, wherein
each of the plurality of magnetic sensor cells further includes a magnetic field generating section that applies to the magnetic sensor a feedback magnetic field that reduces the input magnetic field detected by the magnetic sensor and an output section that outputs an output signal corresponding to a current caused to flow by the magnetic field generating section in order to generate the feedback magnetic field.

6. A measurement apparatus comprising:
a magnetic sensor array that is formed by three-dimensionally arranging a plurality of magnetic sensor cells, and is capable of detecting an input magnetic field in three axial directions;

a measurement data acquiring section that acquires a plurality of measurement values based on the input magnetic field detected by the magnetic sensor array;

a magnetic field calculating section that calculates the input magnetic field based on the plurality of measurement values;

an error calculating section that calculates a detection error of the input magnetic field, based on the plurality of measurement values and a calculation result obtained by calculating the input magnetic field; and a determining section that determines whether to reset at least one magnetic sensor cell among the plurality of magnetic sensor cells, based on the detection error, wherein each of the plurality of magnetic sensor cells includes:
- a magnetic sensor;
- a magnetic field generating section that applies to the magnetic sensor a feedback magnetic field that reduces the input magnetic field detected by the magnetic sensor;
- an output section that outputs an output signal corresponding to a current caused to flow by the magnetic field generating section in order to generate the feedback magnetic field; and
- a magnetic resetting section that, when the magnetic sensor cell is to be reset, applies to the magnetic sensor a reset magnetic field that magnetically saturates the magnetic sensor, wherein the error calculating section calculates the detection error for each of the plurality of measurement values, the determining section makes a determination to reset a magnetic sensor cell, the magnetic sensor cell including a magnetic sensor used to acquire a measurement value for which the detection error is outside a predetermined range, and the magnetic field calculating section recalculates the input magnetic field after the magnetic sensor used to acquire the measurement value for which the detection error is outside the predetermined range has been magnetically reset.

7. The measurement apparatus according to claim 6, wherein the magnetic resetting section includes a switching section that switches whether a feedback current for generating the feedback magnetic field is supplied to the magnetic field generating section, and supplies a reset current to the magnetic field generating section to cause the magnetic field generating section to generate the reset magnetic field in a state where the magnetic field generating section is not supplied with the feedback current.

8. The measurement apparatus according to claim 1, wherein the magnetic field calculating section calculates the input magnetic field in a manner to minimize a square of the detection error.

9. The measurement apparatus according to claim 1, further comprising:

a base vector updating section that updates the base vector based on the detection error.

10. The measurement apparatus according to claim 5, wherein each magnetic sensor includes a magnetoresistance effect element.

11. The measurement apparatus according to claim 10, wherein each magnetic sensor further includes two magnetic flux concentrators arranged at respective ends of the magnetoresistance effect element, and the magnetoresistance effect element is arranged at a position sandwiched between the two magnetic flux concentrators.

12. The measurement apparatus according to claim 11, wherein a coil for generating the feedback magnetic field is wound to surround the magnetoresistance effect element and the two magnetic flux concentrators.

13. The measurement apparatus according to claim 1, further comprising:

a plurality of AD converters that convert outputs of the plurality of magnetic sensor cells from analog to digital, to output the plurality of measurement values, wherein the plurality of AD converters perform AD conversion according to a common sampling clock.

14. The measurement apparatus according to claim 1, wherein a cardiac magnetic field generated by an electrical activity of a heart of an animal is a measurement target, and the cardiac magnetic field is measured based on a calculation result of the magnetic field calculating section.

* * * * *